(12) United States Patent
McCarron et al.

(10) Patent No.: US 9,850,214 B2
(45) Date of Patent: Dec. 26, 2017

(54) INHIBITORS OF NEDD8-ACTIVATING ENZYME

(71) Applicant: Millennium Pharmaceuticals, Inc., Cambridge, MA (US)

(72) Inventors: Ashley Sue McCarron, Bedford, NH (US); Todd B. Sells, Southborough, MA (US); Matthew Stirling, Randolph, MA (US); Stephen G. Stroud, Medford, MA (US)

(73) Assignee: MILLENNIUM PHARMACEUTICALS, INC., Cambridge, MA (US)

( * ) Notice: Subject to any disclaimer, the term of this patent is extended or adjusted under 35 U.S.C. 154(b) by 702 days.

(21) Appl. No.: 14/326,051

(22) Filed: Jul. 8, 2014

(65) Prior Publication Data
US 2015/0011572 A1 Jan. 8, 2015

Related U.S. Application Data

(63) Continuation of application No. 13/592,389, filed on Aug. 23, 2012, now Pat. No. 8,809,356.

(60) Provisional application No. 61/526,830, filed on Aug. 24, 2011.

(51) Int. Cl.
| | | |
|---|---|---|
| *A61K 31/505* | (2006.01) | |
| *C07D 239/02* | (2006.01) | |
| *C07D 239/47* | (2006.01) | |
| *C07D 239/46* | (2006.01) | |
| *C07D 473/02* | (2006.01) | |

(52) U.S. Cl.
CPC ......... *C07D 239/47* (2013.01); *C07D 239/46* (2013.01); *C07D 473/02* (2013.01)

(58) Field of Classification Search
USPC ........................................................ 514/269
See application file for complete search history.

(56) References Cited

U.S. PATENT DOCUMENTS

| | | | |
|---|---|---|---|
| 5,194,446 A | 3/1993 | Lo et al. | |
| 8,008,307 B2 | 8/2011 | Claiborne et al. | |
| 8,207,177 B2 | 6/2012 | Langston et al. | |
| 8,481,550 B2 | 7/2013 | Claiborne et al. | |
| 8,809,356 B2 * | 8/2014 | McCarron ............ | C07D 239/46 514/269 |
| 8,980,850 B2 * | 3/2015 | Smith .................. | A61K 31/706 514/42 |
| 2007/0191293 A1 | 8/2007 | Langston et al. | |
| 2008/0051404 A1 | 2/2008 | Claiborne et al. | |

FOREIGN PATENT DOCUMENTS

| | | |
|---|---|---|
| WO | WO 97/05132 | 2/1997 |
| WO | WO 2004/043955 | 5/2004 |
| WO | WO 2005/037845 | 4/2005 |
| WO | WO 2006/002284 | 1/2006 |
| WO | WO 2006/084281 | 8/2006 |
| WO | WO 2007/092213 | 8/2007 |
| WO | WO 2010/132110 | 11/2010 |

OTHER PUBLICATIONS

Brownell et al., "Substrate-Assisted Inhibition of Ubiquitin-like Protein-Activating Enzymes: The NEDD8 E1 Inhibitor MLN4924 Forms a NEDD8-AMP Mimetic In Situ," *Molecular Cell*, 37: 102-111 (2010).
Extended European Search Report for European Patent Application No. 12825411.7 dated Mar. 25, 2015, (5 pages).
International Search Report and Written Opinion dated Nov. 23, 2007 from International Application No. PCT/US07/017463 corresponding to U.S. Appl. No. 11/890,338.
Gura, Trisha, "Cancer models: systems for identifying new drugs are often faulty," *Science*, vol. 278, No. 5340 (Nov. 7, 1997) pp. 1041-1042.
Johnson, J., et al., "Relationships between drug activity in NCI preclinical in vitro and in vivo models and early clinical trials," *British Journal of Cancer*, vol. 64, No. 10 (2001) pp. 1424-1431.
Simone, Joseph V., *Cecil Textbook of Medicine*, Part XIV, Oncology: Introduction, $20^{th}$ Edition, vol. 1 (1996) pp. 1004-1010.
Xu, G. Wei, et al., "The ubiquitin-activating enzyme E1 as a therapeutic target for the treatment of leukemia and multiple myeloma," *Blood*, vol. 115, No. 11 (Mar. 18, 2010) pp. 2251-2259.
Pearce et al., Failure modes in anticancer drug discovery and development, *Cancer Drug Design and Discovery* Edited by Stephen Neidle, (2008) Chapter 18, pp. 424-435.
Restriction and Election of Species Requirement dated Aug. 31, 2010, in U.S. Appl. No. 11/890,338 (now U.S. Pat. No. 8,008,307).
Non-Final Office Action dated Dec. 9, 2010, in U.S. Appl. No. 11/890,338 (now U.S. Pat. No. 8,008,307).
Notice of Allowability dated Apr. 26, 2011, in U.S. Appl. No. 11/890,338 (now U.S. Pat. No. 8,008,307).
Restriction and Election of Species Requirement dated Jun. 1, 2012, in U.S. Appl. No. 13/216,352 (now U.S. Pat. No. 8,481,550).
Non-Final Office Action dated Nov. 21, 2012, in U.S. Appl. No. 13/216,352 (now U.S. Pat. No. 8,481,550).
Notice of Allowability dated Mar. 7, 2013, in U.S. Appl. No. 13/216,352 (now U.S. Pat. No. 8,481,550).
Non-Final Office Action dated May 23, 2013, in U.S. Appl. No. 13/592,389.
Notice of Allowability dated May 8, 2014, in U.S. Appl. No. 13/592,389.

\* cited by examiner

*Primary Examiner* — Jeffrey S Lundgren
*Assistant Examiner* — Michael Schmitt
(74) *Attorney, Agent, or Firm* — Sterne, Kessler, Goldstein and Fox P.L.L.C.

(57) ABSTRACT

Disclosed are chemical entities which are inhibitors of Nedd8-activating enzyme (NAE), namely, the compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate and pharmaceutically acceptable salts thereof; solid state forms thereof; and prodrugs thereof. Also disclosed are methods of using the chemical entities to treat disorders such as cancer.

15 Claims, 10 Drawing Sheets

PK Parameters of K-I-115 in Female Ncr Nude Mice
Bearing HCT 116 Tumor Xenografts
Following a Single Subcutaneous Administration at 30 mg/kg.

| Sample | AUC last (nM*hr) | Cmax (nM) |
|---|---|---|
| Plasma | 26271 | 27138 |

INHIBITORS OF NEDD8-ACTIVATING ENZYME

PRIORITY CLAIM

This is a continuation of U.S. patent application Ser. No. 13/592,389, filed Aug. 23, 2012, which claims the benefit under 35 U.S.C. §119(e) of U.S. Provisional patent application Ser. No. 61/526,830, filed Aug. 24, 2011, each of which is hereby incorporated by reference in its entirety.

FIELD

This invention relates to compounds, compositions and methods for the treatment of various disorders, particularly disorders of cell proliferation, including cancers, and inflammatory disorders. In particular, the invention provides compounds which inhibit the activity of NEDD8-activating enzyme.

BACKGROUND

The post-translational modification of proteins by ubiquitin-like molecules (ubls) is an important regulatory process within cells, playing key roles in controlling many biological processes including cell division, cell signaling and the immune response. Ubls are small proteins that are covalently attached to a lysine on a target protein via an isopeptide linkage with a C-terminal glycine of the ubl. The ubiquitin-like molecule alters the molecular surface of the target protein and can affect such properties as protein-protein interactions, enzymatic activity, stability and cellular localization of the target.

Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein.

The biological consequence of ubl modification depends on the target in question. Ubiquitin is the best characterized of the ubls and a consequence of modification by ubiquitination is the degradation of poly-ubiquitinated proteins by the 26S proteasome. Ubiquitin is conjugated to its target proteins through an enzymatic cascade involving its specific E1 activating enzyme, Uba1 (ubiquitin activating enzyme, UAE), a conjugating enzyme from the family of E2s, and a ubiquitin ligase from either the RING or HECT classes of E3s. See, Huang et al., *Oncogene*, 23:1958-71 (2004). Target specificity is controlled by the particular combination of E2 and E3 protein, with >40 E2s and >100 E3s being known at present. In addition to ubiquitin, there are at least 10 ubiquitin-like proteins, each believed to be activated by a specific E1 activating enzyme and processed through similar but distinct downstream conjugation pathways. Other ubls for which E1 activating enzymes have been identified include Nedd8 (APPBP1-Uba3), ISG15 (UBE1L) and the SUMO family (Aos1-Uba2).

The ubl Nedd8 is activated by the heterodimer Nedd8-activating enzyme (APPBP1-Uba3) (NAE) and is transferred to a single E2 (Ubc12), ultimately resulting in ligation to cullin proteins. The function of neddylation is the activation of cullin-based ubiquitin ligases involved in the ubiquitination and hence turnover of many cell cycle and cell signaling proteins, including p27 and I-κB. See Pan of al., *Oncogene*. 23:1985-97 (2004). The ubl SUMO is activated by the heterodimer sumo activating enzyme (Aos1-Uba2) (SAE) and is transferred to a single E2 (Ubc9), followed by coordination with multiple E3 ligases, ultimately resulting in sumoylation of target proteins. Sumo modification can affect the cellular localization of target proteins and proteins modified by SUMO family members are involved in nuclear transport, signal transduction and the stress response. See Seeler and Dejean, *Nat Rev Mol Cell Biol*. 4:690-9, (2003). The function of sumoylation includes activation of cell signaling pathways (e.g., cytokine, WNT, growth factor, and steroid hormone signaling) involved in transcription regulation; as well as pathways involved in control of genomic integrity (e.g., DNA replication, response to DNA damage, recombination and repair). See Muller et al, *Oncogene*. 23:1998-2006, (2004). There are other ubls (e.g., ISG15, FAT10, Apg12p) for which the biological functions are still under investigation.

A particular pathway of importance which is regulated via E1 activating enzyme activities is the ubiquitin-proteasome pathway (UPP). As discussed above, the enzymes UAE and NAE regulate the UPP at two different steps in the ubiquitination cascade. UAE activates ubiquitin in the first step of the cascade, while NAE, via activation of Nedd8, is responsible for the activation of the cullin based ligases, which in turn are required for the final transfer of ubiquitin to certain target proteins. A functional UPP pathway is required for normal cell maintenance. The UPP plays a central role in the turnover of many key regulatory proteins involved in transcription, cell cycle progression and apoptosis, all of which are important in disease states, including tumor cells. See, e.g., King et al., *Science* 274: 1652-1659 (1996); Vorhees et al., *Clin. Cancer Res.*, 9: 6316-6325 (2003); and Adams et al., *Nat. Rev. Cancer*, 4: 349-360 (2004). Proliferating cells are particularly sensitive to inhibition of the UPP. See, Drexler, *Proc. Natl. Acad. Sci., USA* 94: 855-860 (1977). The role of the UPP pathway in oncogenesis has led to the investigation of proteasome inhibition as a potential anticancer therapy. For example, modulation of the UPP pathway by inhibition of the 26S proteasome by VELCADE® (bortezomib) has proven to be an effective treatment in certain cancers and is approved for the treatment of multiple myeloma and mantle cell lymphoma patients who have received at least one prior therapy. Examples of proteins whose levels are controlled by cullin-based ubiquitin ligases which are downstream of NAE and UAE activity include the CDK inhibitor p27$^{Kip1}$ and the inhibitor of NFκB, IκB. See, Podust at al., *Proc. Natl. Acad. Sci.*, 97: 4579-4584 (2000), and Read at al., *Mol. Cell Biol.*, 20: 2326-2333 (2000). Inhibition of the degradation of p27 is expected to block the progression of cells through the G1 and S phases of the cell cycle. Interfering with the degradation of IκB should prevent the nuclear localization of NF-κB, transcription of various NF-κB-dependent genes associated with the malignant phenotype, and resistance to standard cytotoxic therapies. Additionally, NF-κB plays a key role in the expression of a number of pro-inflammatory mediators, implicating a role for such inhibitors in inflammatory diseases. Furthermore, inhibition of UPP has been implicated as a useful target for additional therapeutics, such as inflammatory disorders, including, e.g., rheumatoid arthritis, asthma, multiple sclerosis, psoriasis and reperfusion injury; neurodegenerative disorders, including, e.g., Parkinson's disease, Alzheimer's disease, triplet repeat disorders; neuropathic pain; ischemic disorders, e.g., stroke, infarction, kidney disorders; and cachexia. See, e.g., Elliott and Ross, *Am. J. Clin. Pathol.*, 116:637-46 (2001); Elliott at al., *J. Mol. Med.*, 81:235-45 (2003); Tarlac and Storey, *J. Neurosci. Res.* 74: 406-416 (2003); Mori at al., *Neuropath. Appl. Neurobiol.*, 31: 53-61 (2005); Manning, *Curr. Pain Headache Rep.*, 8: 192-8 (2004); Dawson and Dawson, *Science*, 302: 819-822 (2003); Kukan, *J. Physiol. Pharmacol.*, 55: 3-15 (2004); Wojcik and DiNapoli, *Stroke*, 35:1506-18 (2004); Lazarus at al., *Am J Physiol.*, 27:E332-41 (1999).

Targeting E1 activating enzymes provides a unique opportunity to interfere with a variety of biochemical pathways important for maintaining the integrity of cell division and cell signaling. E1 activating enzymes function at the first step of ubl conjugation pathways; thus, inhibition of an E1 activating enzyme will specifically modulate the downstream biological consequences of the ubl modification. As such, inhibition of these activating enzymes, and the resultant inhibition of downstream effects of ubl-conjugation, represents a method of interfering with the integrity of cell division, cell signaling, and several aspects of cellular physiology which are important for disease mechanisms. Thus, E1 enzymes such as UAE, NAE, and SAE, as regulators of diverse cellular functions, are potentially important therapeutic targets for the identification of novel approaches to treatment of diseases and disorders.

U.S. patent application Ser. No. 11/346,469 (filed Feb. 2, 2006, publication no. US 2006/0189636) and International Patent Appl. No. PCT/US06/04637 (filed Feb. 2, 2006, publication no. WO 2006/084281) (collectively, "Critchley et al.") report various E1 enzyme inhibitors of the formula:

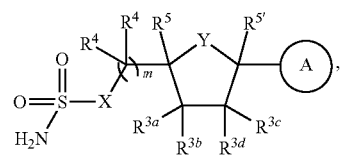

wherein:
A is

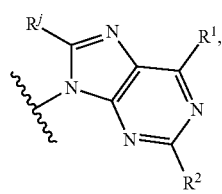
A-i

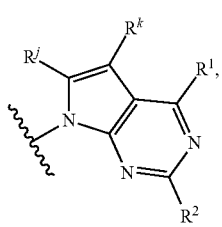
A-ii

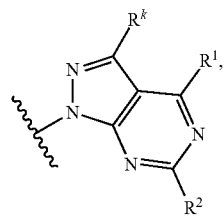
A-iii

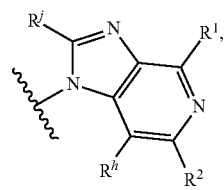
A-iv

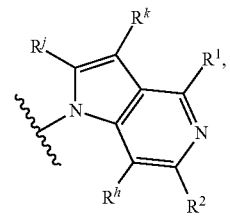
A-v

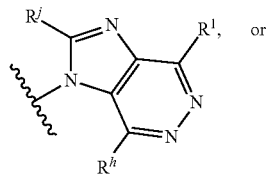
A-vi or

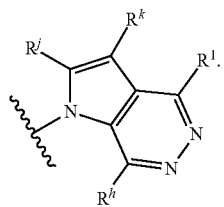
A-vii

These applications do not report the chemical entities that are the subject of this application.

U.S. patent application Ser. No. 11/700,614 (filed Jan. 31, 2007, publication no. US 2007/0191293) and International Patent Appl. No. PCT/US07/02560 (filed Jan. 31, 2007, publication no. WO 2007/092213) (collectively, "Langston et al.") report various E1 enzyme inhibitors of the formula:

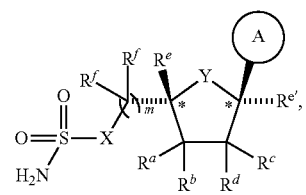

wherein:
A is

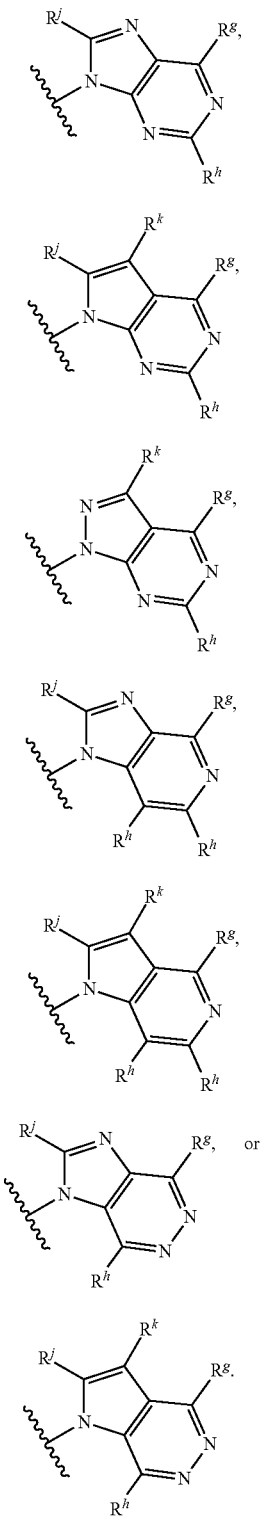

These applications do not report the chemical entities that are the subject of this application.

U.S. patent application Ser. No. 11/890,338 (filed Aug. 6, 2007, publication no. US 2008/0051404) and International Patent Appl. No. PCT/US07/17463 (filed Aug. 6, 2007, publication no. WO 2008/019124) (collectively, "Claiborne et al.") report various E1 enzyme inhibitors of the formula:

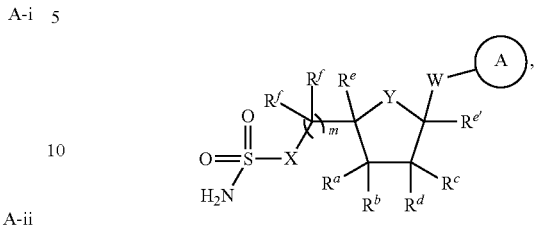

wherein:
Ring A is a 6-membered nitrogen-containing heteroaryl ring, optionally fused to a 5- or 6-membered aryl, heteroaryl, cycloaliphatic or heterocyclic ring; and W is —$CH_2$—, —CHF—, —$CF_2$—, —CH($R^1$)—, —CF($R^1$)—, —NH—, —N($R^1$)—, —O—, —S— or —NHC(O)—.

These applications do not report the chemical entities that are the subject of this application.

At this time, no inhibitor of an E1 activating enzyme has been approved as a treatment by a government health authority. A need continues to exist for inhibitors of E1 activating enzymes such as NAE.

SUMMARY

In one aspect, the invention relates to the chemical entities which are the compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) and pharmaceutically acceptable salts thereof, and prodrugs thereof.

In one aspect, the invention relates to compositions comprising the chemical entity which is the compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) or a pharmaceutically acceptable salt thereof, or a prodrug thereof, and one or more pharmaceutically acceptable carriers.

In one aspect, the invention relates to solid state forms of the compound {(1S,2S,4R)-4-[(6-{[(1R,2S)-5-chloro-2-methoxy-2,3-dihydro-1H-inden-1-yl]amino}pyrimidin-44)oxy]-2-hydroxycyclopentyl}methyl sulfamate (I-216) or a pharmaceutically acceptable salt thereof.

In one aspect, the invention relates to methods of treating cancer comprising administering to a patient in need of such treatment the chemical entity which is the compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) or a pharmaceutically acceptable salt thereof, or a prodrug thereof.

BRIEF DESCRIPTION OF THE FIGURES

FIG. 2 shows the pharmacodynamic and pharmcokinetic parameters for {(1S,2S,4R)-4-[(6-{[(1R,2S)-5-chloro-2- methoxy-2,3-dihydro-1H-inden-1-yl]amino}pyrimidin-4-yl)oxy]-2-hydroxycyclopentyl}methyl sulfamate (I-216) in female Ncr nude mice bearing HCT116 tumor xenografts following a single subcutaneous administration at 10 mg/kg.

Figure 3:
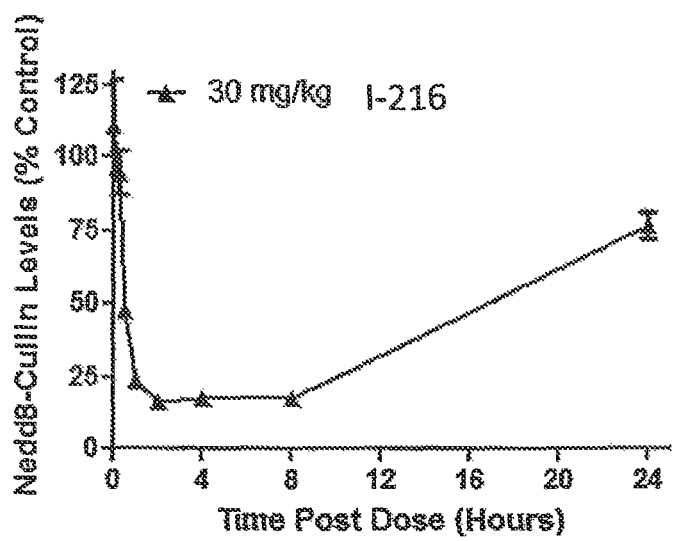

FIG. 3 shows the pharmacokinetic and pharmcokinetic parameters for {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) in female Ncr nude mice bearing HCT116 tumor xenografts following a single subcutaneous administration at 30 mg/kg.

Figure 4:
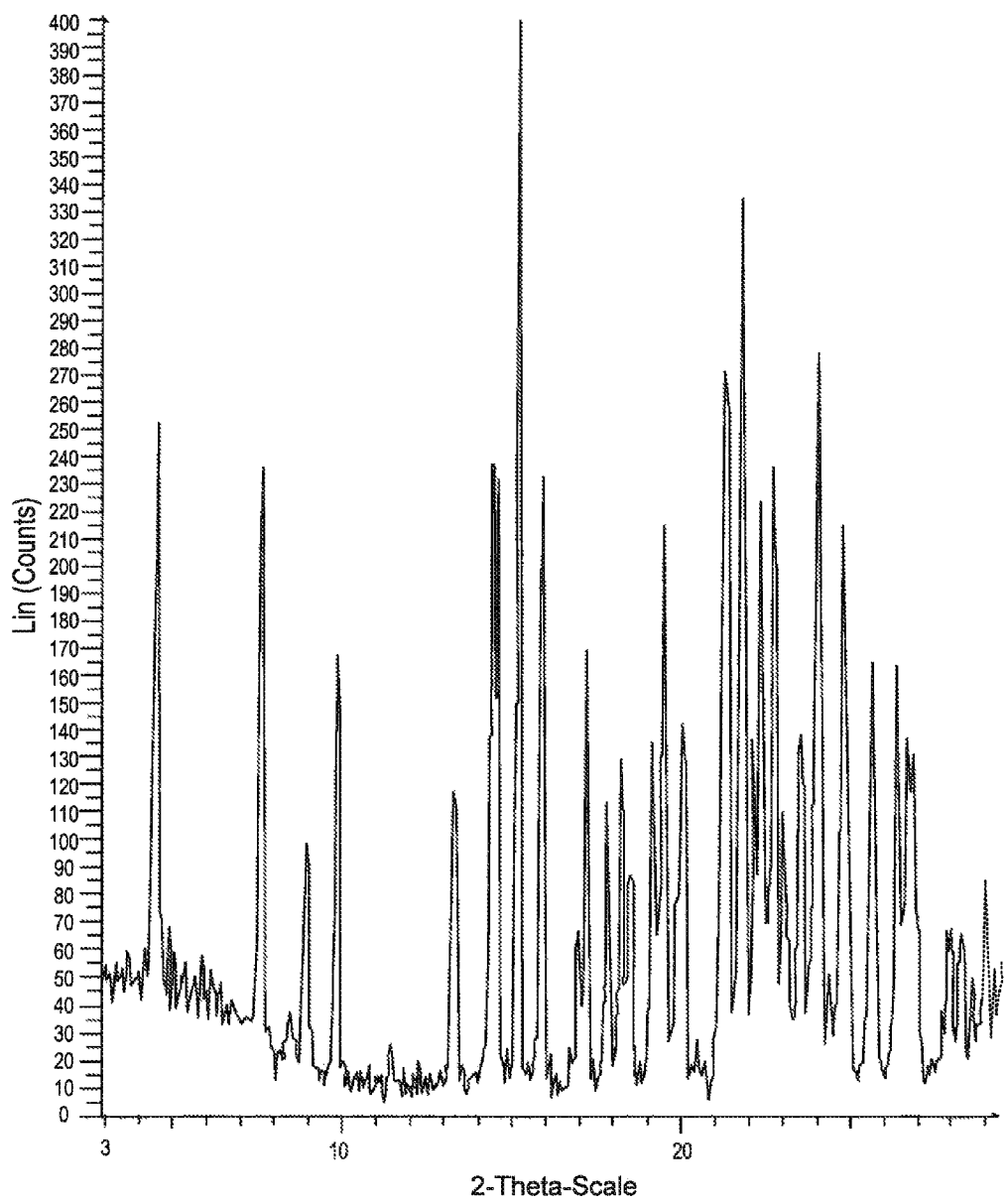

FIG. 4 shows an x-ray powder diffraction (XRPD) pattern for crystalline Form I {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) hydrochloride.

Figure 5:
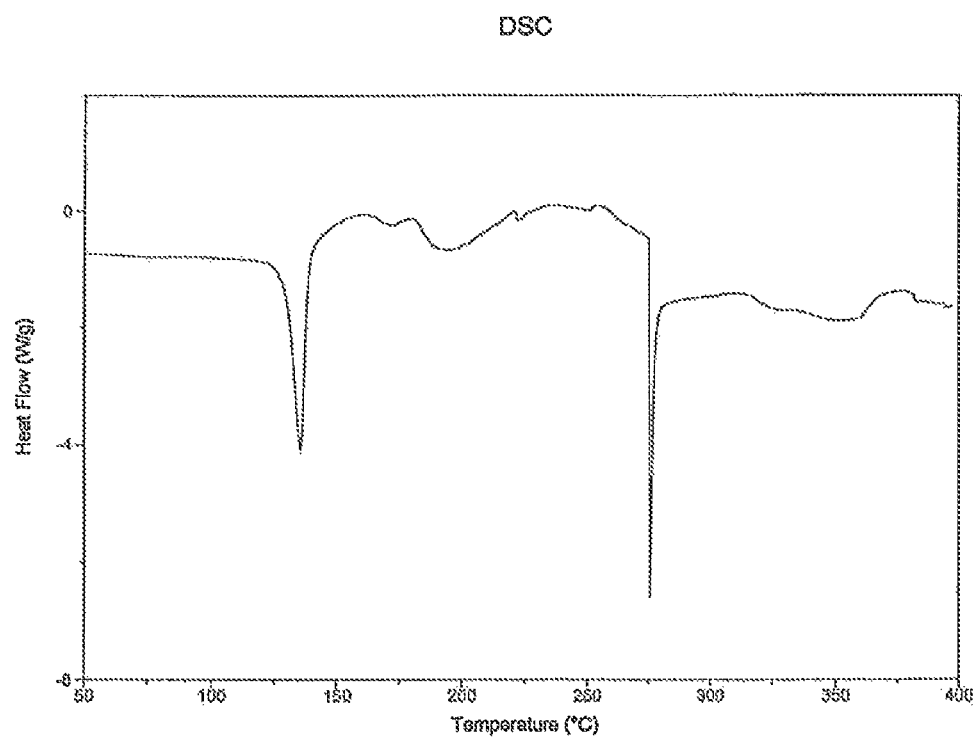

FIG. 5 shows a differential scanning calorimetry (DSC) thermogram for crystalline Form I {(1S,2S,4R)-4-[(6-{[(1R,2S)-5-chloro-2-methoxy-2,3-dihydro-1H-inden-1-yl]amino}-pyrimidin-4-yl)oxy]-2-hydroxycyclopentyl}methyl sulfamate (I-216) hydrochloride.

Figure 6:
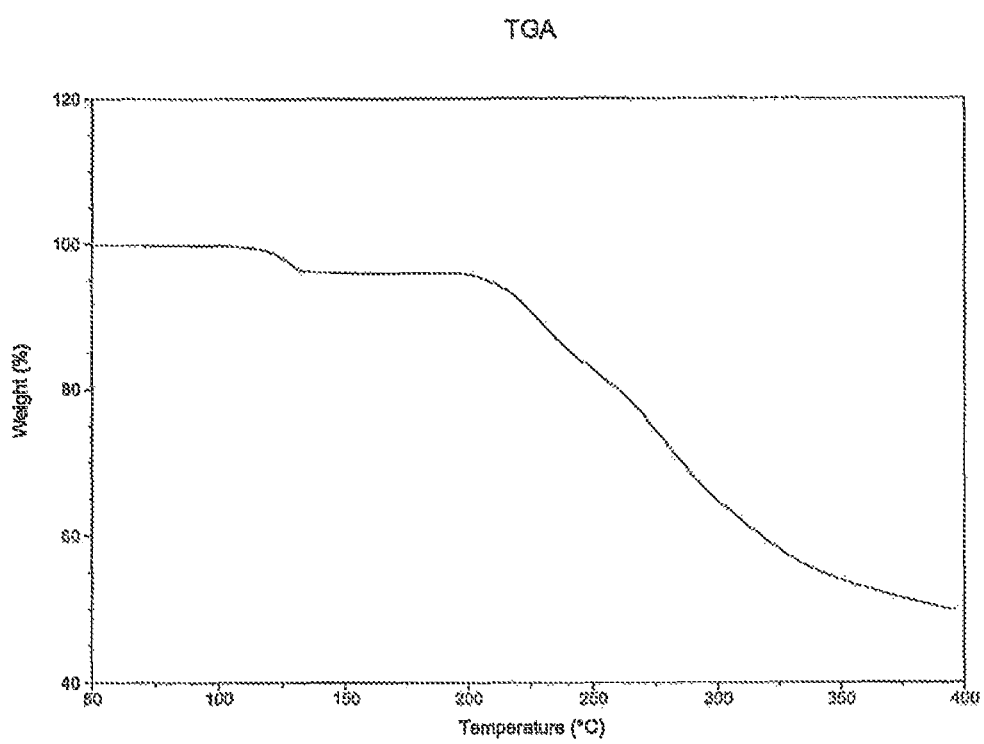

FIG. 6 shows a thermogravimetric analysis (TGA) thermogram for crystalline Form I {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) hydrochloride.

Figure 7:
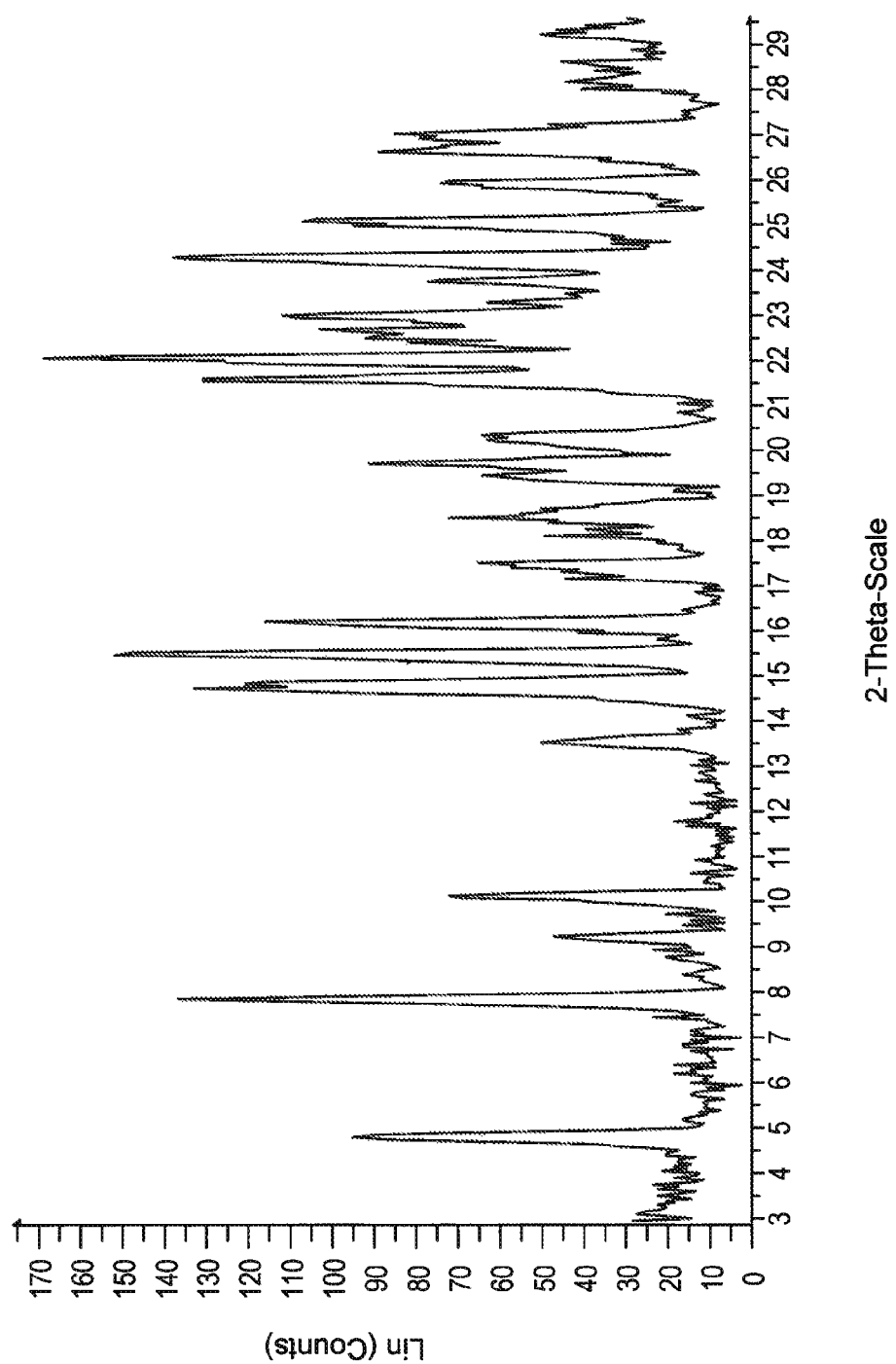

FIG. 7 shows an x-ray powder diffraction (XRPD) pattern for crystalline Form I {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) hydrochloride produced in Example 2, below.

Figure 8:
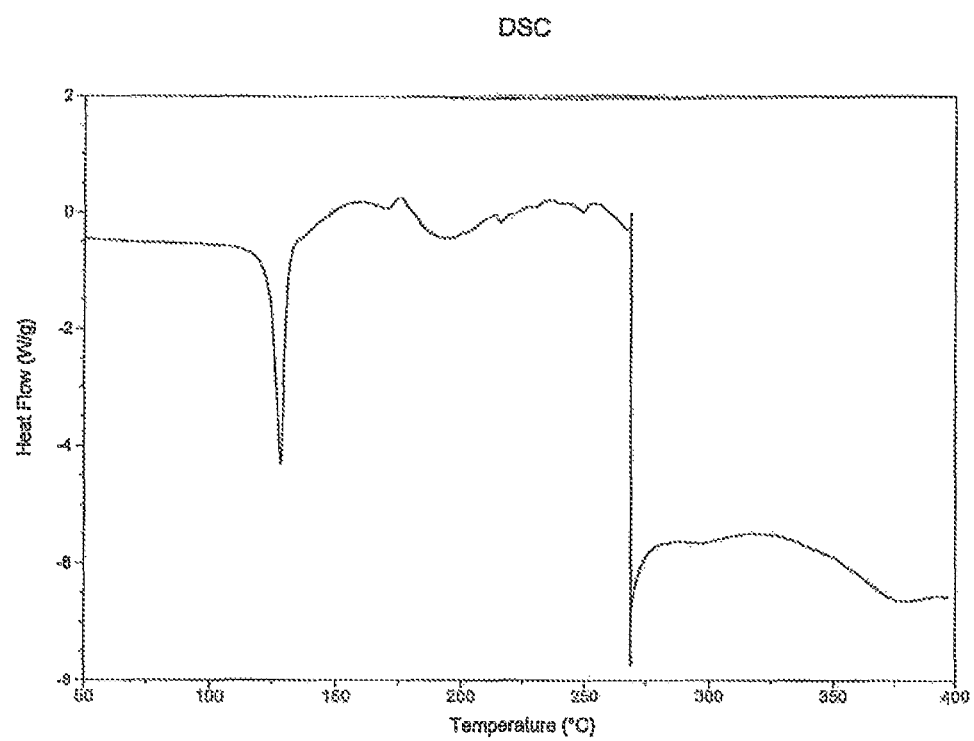

FIG. 8 shows a differential scanning calorimetry (DSC) thermogram for crystalline Form I {(1S,2S,4R)-4-[(6-{[(1R,2S)-5-chloro-2-methoxy-2,3-dihydro-1H-inden-1-yl]amino}-pyrimidin-4-yl)oxy]-2-hydroxycyclopentyl}methyl sulfamate (I-216) hydrochloride produced in Example 2, below.

Figure 9:
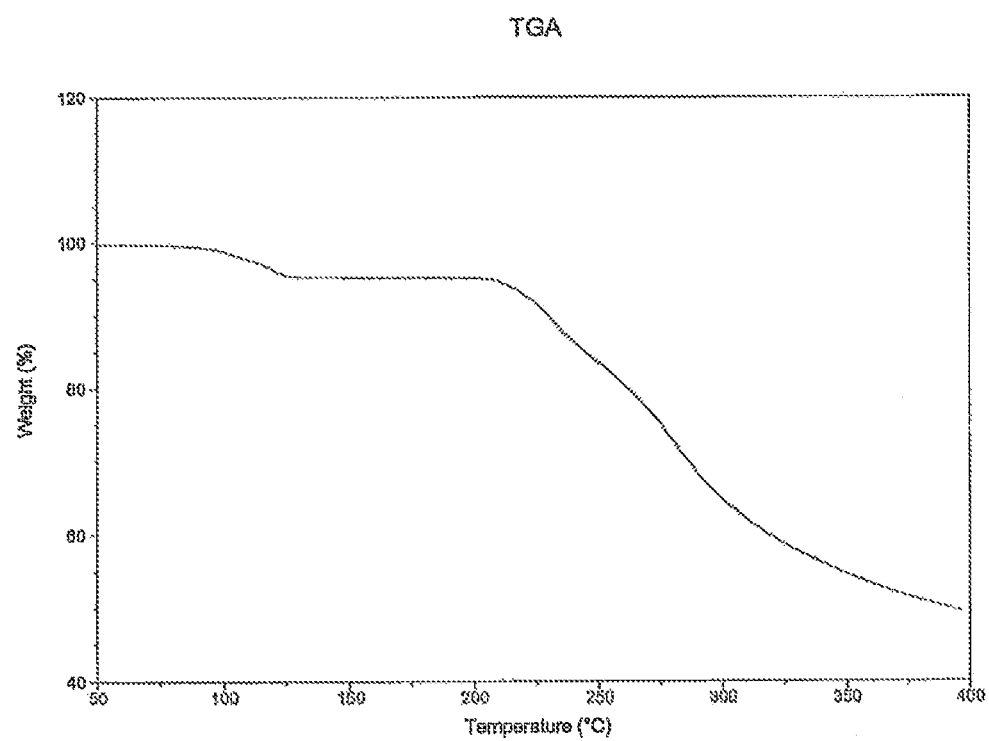

FIG. 9 shows a thermogravimetric analysis (TGA) thermogram for crystalline Form I {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) hydrochloride produced in Example 2, below.

Figure 10:
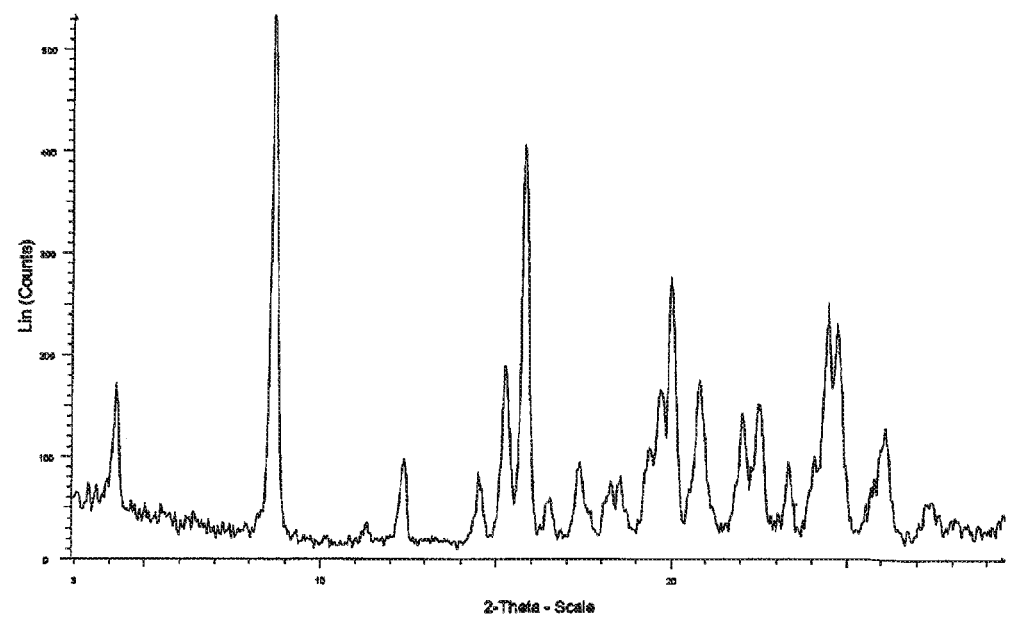

FIG. 10 shows an x-ray powder diffraction (XRPD) pattern for crystalline Form II {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) hydrochloride produced in Example 9, below.

DESCRIPTION

Provided are chemical entities that are effective as inhibitors of Nedd8-activating enzyme (NAE). The chemical entities are useful for inhibiting NAE activity in vitro and in vivo, and are useful for the treatment of disorders of cell proliferation, particularly cancers, and other disorders associated with NAE activity. The chemical entities are the compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (herein referred to as "I-216"):

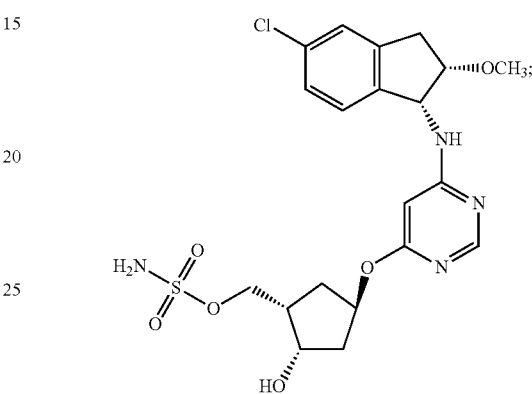

and non-covalently associated molecular entities. A chemical entity comprising the compound I-216 thus includes, e.g., the free compound I-216, pharmaceutically acceptable salts of I-216, pharmaceutically acceptable solvates of I-216 and pharmaceutically acceptable solvates of pharmaceutically acceptable salts of I-216. In some embodiments, the chemical entity is the free compound I-216 or a pharmaceutically acceptable salt thereof. In some embodiments, the chemical entity is a pharmaceutically acceptable salt of I-216. In some embodiments, the chemical entity is the free compound I-216 or a pharmaceutically acceptable solvate thereof. In some embodiments, the chemical entity is a pharmaceutically acceptable solvate of a pharmaceutically acceptable salt of I-216.

Claiborne et al. report various inhibitors of E1 enzymes, including NAE. For example, Claiborne et al. report that the compounds in the following Table 1 exhibited $IC_{50}$ values less than or equal to 500 nM in an NAE assay (Claiborne Example 137).

TABLE 1

| | |
|---|---|
| I-1 | {(1R,2R,3S,4R)-4-[(6-{[(1S)-4-fluoro-2,3-dihydro-1H-inden-1-yl]amino}pyrimidin-4-yl)-amino]-2,3-dihydroxycyclopentyl}methyl sulfamate; |
| I-2 | {(1R,2R,3S,4R)-2,3-dihydroxy-4-[(6-{[(1R,2S)-2-methoxy-2,3-dihydro-1H-inden-1-yl]-amino}pyrimidin-4-yl)amino]cyclopentyl}methyl sulfamate; |
| I-3 | [(1R,2R,3S,4R)-2,3-dihydroxy-4-(9H-purin-6-ylamino)cyclopentyl]methyl sulfamate; |
| I-5 | [(1S,2S,4R)-4-({6-[(1S)-2,3-dihydro-1H-inden-1-ylamino]pyrimidin-4-yl}amino)-2-hydroxycyclopentyl]methyl sulfamate; |
| I-6 | {(1R,2R,3S,4R)-4-[(6-{[(1S)-4,7-difluoro-2,3-dihydro-1H-inden-1-yl]amino}pyrimidin-4-yl)amino]-2,3-dihydroxycyclopentyl}methyl sulfamate; |
| I-8 | [(1R,2R,3S,4R)-4-({6-[(1R)-2,3-dihydro-1H-inden-1-ylamino]pyrimidin-4-yl}amino)-2,3-dihydroxycyclopentyl]methyl sulfamate; |
| I-9 | {(1R,2R,3S,4R)-2,3-dihydroxy-4-[(8-phenyl-9H-purin-6-yl)amino]cyclopentyl}methyl sulfamate; |
| I-10 | [(1R,2R,3S,4R)-2,3-dihydroxy-4-({2-[(3-methyl-2,3-dihydro-1H-inden-1-yl)-amino]pyrimidin-4-yl}amino)cyclopentyl]methyl sulfamate; |
| I-11 | [(1S,2R,3S,4R)-4-({6-[(1S)-2,3-dihydro-1H-inden-1-ylamino]pyrimidin-4-yl}amino)-2,3-dihydroxycyclopentyl]methyl sulfamate; |

TABLE 1-continued

| | |
|---|---|
| I-12 | [(1R,2R,3S,4R)-2,3-dihydroxy-4-({6-[(1S)-1,2,3,4-tetrahydronaphthalen-1-ylamino]pyrimidin-4-yl}amino)cyclopentyl]methyl sulfamate; |
| I-14 | [(1R,2R,3S,4R)-4-({6-[(cyclohexylmethyl)amino]pyrimidin-4-yl}amino)-2,3-dihydroxycyclopentyl]methyl sulfamate; |
| I-15 | {(1R,2R,3S,4R)-4-[(2-{[(1S)-3,3-dimethyl-2,3-dihydro-1H-inden-1-yl]amino}pyrimidin-4-yl)amino]-2,3-dihydroxycyclopentyl}methyl sulfamate; |
| I-17 | {(1R,2R,3S,4R)-4-[(6-{[(1S)-5,6-difluoro-2,3-dihydro-1H-inden-1-yl]amino}pyrimidin-4-yl)amino]-2,3-dihydroxycyclopentyl}methyl sulfamate; |
| I-18 | [(1R,2R,3S,4R)-4-({6-[(1S)-2,3-dihydro-1H-inden-1-ylamino]-2-methylpyrimidin-4-yl}amino)-2,3-dihydroxycyclopentyl]methyl sulfamate; |
| I-19 | {(1R,2R,3S,4R)-4-[(6-{[(1S)-5-chloro-2,3-dihydro-1H-inden-1-yl]amino}pyrimidin-4-yl)amino]-2,3-dihydroxycyclopentyl}methyl sulfamate; |
| I-21 | {(1R,2R,3S,4R)-4-[(6-{[(1S)-3,3-dimethyl-2,3-dihydro-1H-inden-1-yl]amino}pyrimidin-4-yl)amino]-2,3-dihydroxycyclopentyl}methyl sulfamate; |
| I-24 | {(1R,2R,3S,4R)-4-[(6-{[(1S)-4-chloro-2,3-dihydro-1H-inden-1-yl]amino}pyrimidin-4-yl)amino]-2,3-dihydroxycyclopentyl}methyl sulfamate; |
| I-25 | [(1R,2S,4R)-4-({6-[(1S)-2,3-dihydro-1H-inden-1-ylamino]pyrimidin-4-yl}amino)-2-hydroxycyclopentyl]methyl sulfamate; |
| I-26 | [(1R,2R,3S,4R)-4-({4-[(1S)-2,3-dihydro-1H-inden-1-ylamino]-1,3,5-triazin-2-yl}amino)-2,3-dihydroxycyclopentyl]methyl sulfamate; |
| I-27 | ((1R,2R,3S,4R)-4-{[6-(benzylamino)pyrimidin-4-yl]amino}-2,3-dihydroxycyclopentyl)-methyl sulfamate; |
| I-29 | [(1R,2R,3S,4R)-4-({6-[(1S)-2,3-dihydro-1H-inden-1-ylamino]pyrimidin-4-yl}amino)-2,3-dihydroxycyclopentyl]methyl sulfamate; |
| I-32 | [(1S,2S,4R)-4-({6-[(1S)-2,3-dihydro-1H-inden-1-ylamino]-5-methylpyrimidin-4-yl}oxy)-2-hydroxycyclopentyl]methyl sulfamate; |
| I-34 | ((1S,2S,4R)-4-{[8-(2-chlorophenyl)-9H-purin-6-yl]amino}-2-hydroxycyclopentyl)methyl sulfamate; |
| I-37 | ((1S,2S,4R)-2-hydroxy-4-{[8-(2-phenoxyphenyl)-9H-purin-6-yl]amino}cyclopentyl)methyl sulfamate; |
| I-38 | {(1S,2S,4R)-2-hydroxy-4-[(6-phenyl-7H-pyrrolo[2,3-d]pyrimidin-4-yl)amino]cyclopentyl}methyl sulfamate; |
| I-39 | {(1S,2S,4R)-4-[(8-dibenzo[b,d]furan-4-yl-9H-purin-6-yl)amino]-2-hydroxycyclopentyl}methyl sulfamate; |
| I-40 | [(1S,2S,4R)-2-hydroxy-4-({6-[(1S)-1,2,3,4-tetrahydronaphthalen-1-ylamino]pyrimidin-4-yl}oxy)cyclopentyl]methyl sulfamate; |
| I-41 | ((1S,2S,4R)-4-{[8-(2,3-dihydro-1,4-benzodioxin-5-yl)-9H-purin-6-yl]amino}-2-hydroxycyclopentyl)methyl sulfamate; |
| I-42 | [(1S,2S,4R)-2-hydroxy-4-({6-[(1-naphthylmethyl)amino]pyrimidin-4-yl}oxy)cyclopentyl]methyl sulfamate; |
| I-43 | {(1S,2S,4R)-2-hydroxy-4-[(6-{[(1S,2S)-2-methyl-2,3-dihydro-1H-inden-1-yl]amino}pyrimidin-4-yl)oxy]cyclopentyl}methyl sulfamate; |
| I-45 | [(1R,2R,3S,4R)-4-({4-[(1S)-2,3-dihydro-1H-inden-1-ylamino]-6-methyl-1,3,5-triazin-2-yl}amino)-2,3-dihydroxycyclopentyl]methyl sulfamate; |
| I-46 | ((1S,2S,4R)-2-hydroxy-4-{methyl[8-(1-naphthyl)-9H-purin-6-yl]amino}cyclopentyl)methyl sulfamate; |
| I-47 | {(1S,2S,4R)-2-hydroxy-4-[(6-{[(1R,2S)-2-methoxy-2,3-dihydro-1H-inden-1-yl]amino}pyrimidin-4-yl)amino]cyclopentyl}methyl sulfamate; |
| I-49 | ((1S,2S,4R)-2-hydroxy-4-{[8-(1-naphthyl)-9H-purin-6-yl]amino}cyclopentyl)methyl sulfamate; |
| I-55 | {(1R,2R,3S,4R)-2,3-dihydroxy-4-[(4-{[(1R,2S)-2-methoxy-2,3-dihydro-1H-inden-1-yl]amino}-1,3,5-triazin-2-yl)amino]cyclopentyl}methyl sulfamate; |
| I-56 | ((1S,2S,4R)-4-{[6-chloro-2-(1-naphthyl)-3H-imidazo[4,5-b]pyridin-7-yl]amino}-2-hydroxycyclopentyl)methyl sulfamate; |
| I-60 | ((1S,2S,4R)-4-{[8-(3-chlorophenyl)-9H-purin-6-yl]amino}-2-hydroxycyclopentyl)methyl sulfamate; |
| I-62 | [(1S,2S,4R)-2-hydroxy-4-({8-[2-(trifluoromethoxy)phenyl]-9H-purin-6-yl}amino)cyclopentyl]methyl sulfamate; |
| I-63 | {(1S,2S,4R)-2-hydroxy-4-[(8-phenyl-9H-purin-6-yl)oxy]cyclopentyl}methyl sulfamate; |
| I-64 | [(1S,2S,4R)-4-({8-[4-(dimethylamino)-1-naphthyl]-9H-purin-6-yl}amino)-2-hydroxycyclopentyl]methyl sulfamate; |
| I-65 | {(1S,2S,4R)-4-[(6-{[(1S)-3,3-dimethyl-2,3-dihydro-1H-inden-1-yl]amino}pyrimidin-4-yl)amino]-2-hydroxycyclopentyl}methyl sulfamate; |
| I-67 | ((1S,2S,4R)-8-{[8-(2,3-dimethoxyphenyl)-9H-purin-6-yl]amino}-2-hydroxycyclopentyl)methyl sulfamate; |
| I-68 | [(1S,2S,4R)-4-({8-[2-(benzyloxy)phenyl]-9H-purin-6-yl}amino)-2-hydroxycyclopentyl]methyl sulfamate; |
| I-69 | {(1S,2S,4R)-2-hydroxy-4-[(8-phenyl-9H-purin-6-yl)amino]cyclopentyl}methyl sulfamate; |
| I-71 | {(1S,2S,4R)-4-[(6-{[(1S)-3,3-dimethyl-2,3-dihydro-1H-inden-1-yl]amino}-5-fluoropyrimidin-4-yl)amino]-2-hydroxycyclopentyl}methyl sulfamate; |
| I-73 | ((1S,2S,4R)-4-{[8-(7-chloroquinolin-4-yl)-7H-purin-6-yl]oxy}-2-hydroxycyclopentyl)methyl sulfamate; |
| I-74 | ((1S,2S,4R)-2-hydroxy-4-{[6-(1-naphthyl)-7H-pyrrolo[2,3-d]pyrimidin-4-yl]amino}cyclopentyl)methyl sulfamate; |
| I-82 | N-({(1S,2S,4R)-2-hydroxy-4-[(6-{[(1R,2S)-2-methoxy-2,3-dihydro-1H-inden-1-yl]amino}pyrimidin-4-yl)oxy]cyclopentyl}methyl)sulfamide |
| I-83 | {(1S,2S,4R)-4-[(5-fluoro-6-{[(1R,2S)-2-methoxy-2,3-dihydro-1H-inden-1-yl]amino}pyrimidin-4-yl)oxy]-2-hydroxycyclopentyl}methyl sulfamate; |

TABLE 1-continued

| | |
|---|---|
| I-84 | {(1S,2S,4R)-2-hydroxy-4-[(8-quinolin-8-yl-7H-purin-6-yl)amino]cyclopentyl}methyl sulfamate; |
| I-87 | ((1S,2S,4R)-2-hydroxy-4-{[8-(1-naphthyl)-9H-purin-8-yl]oxy}cyclopentyl)methyl sulfamate; |
| I-88 | {(1S,2S,4R)-4-[(8-benzyl-9H-purin-6-yl)amino]-2-hydroxycyclopentyl}methyl sulfamate; |
| I-90 | {(1S,2S,4R)-2-hydroxy-4-[(2-phenyl[1,3]oxazolo[5,4-d]pyrimidin-7-yl)amino]cyclopentyl}methyl sulfamate; |
| I-93 | ((1S,2S,4R)-4-{[8-(2,6-dimethoxyphenyl)-9H-purin-6-yl]amino}-2-hydroxycyclopentyl)methyl sulfamate; |
| I-99 | ((1S,2S,4R)-2-hydroxy-4-{[8-(3-methoxyphenyl)-9H-purin-6-yl]amino}cyclopentyl)methyl sulfamate; |
| I-100 | ((1S,2S,4R)-4-{[8-(2,2-dimethyl-2,3-dihydro-1-benzofuran-7-yl)-9H-purin-6-yl]amino}-2-hydroxycyclopentyl)methyl sulfamate; |
| I-101 | [(1S,2S,4R)-2-hydroxy-4-({8-[(3-methylphenyl)sulfonyl]-9H-purin-6-yl}oxy)cyclopentyl]methyl sulfamate; |
| I-102 | [{1S,2S,4R)-4-({8-[4-(benzyloxy)phenyl]-7H-purin-6-yl}amino)-2-hydroxycyclopentyl]methyl sulfamate; |
| I-103 | [(1S,2S,4R)-4-({8-[4-(dimethylamino)-1-naphthyl]-7H-purin-6-yl}oxy)-2-hydroxycyclopentyl]methyl sulfamate; |
| I-105 | {(1S,2S,4R)-4-[(8-biphenyl-3-yl-9H-purin-6-yl}amino]-2-hydroxycyclopentyl}methyl sulfamate; |
| I-106 | {(1R,2R,3S,4R)-4-[{6-[(1S)-2,3-dihydro-1H-inden-1-ylamino]pyrimidin-4-yl}(methyl)amino]-2,3-dihydroxycyclopentyl}methyl sulfamate; |
| I-107 | ((1S,2S,4R)-2-hydroxy-4-{[8-(2-methylphenyl)-9H-purin-6-yl]amino}cyclopentyl)methyl sulfamate; |
| I-108 | ((1R,2R,3S,4R)-2,3-dihydroxy-4-{[6-(phenylethynyl)pyrimidin-4-yl]amino}cyclopentyl)methyl sulfamate; |
| I-109 | ((1S,2S,4R)-2-hydroxy-4-{[2-(1-naphthyl)-3H-imidazo[4,5-b]pyridin-7-yl]oxy}cyclopentyl)methyl sulfamate; |
| I-111 | ((1S,2S,4R)-4-{[8-{4-chlorophenyl)-9H-purin-6-yl]amino}-2-hydroxycyclopentyl)methyl sulfamate; |
| I-112 | {(1S,2S,4R)-2-hydroxy-4-[(8-isoquinolin-4-yl-7H-purin-6-yl)oxy]cyclopentyl}methyl sulfamate; |
| I-115 | {(1S,2S,4R)-2-hydroxy-4-[(6-{[(1R,2S)-2-methoxy-2,3-dihydro-1H-inden-1-yl]amino}pyrimidin-4-yl)oxy]cyclopentyl}methyl sulfamate; |
| I-117 | ((1S,2S,4R)-4-{[8-(2,3-dihydro-1-benzofuran-7-yl)-7H-purin-6-yl]amino}-2-hydroxycyclopentyl)methyl sulfamate; |
| I-118 | ((1R,2R,3S,4R)-2,3-dihydroxy-4-{[6-(5,6,7,8-tetrahydronaphthalen-1-ylamino)pyrimidin-4-yl]amino}cyclopentyl)methyl sulfamate; |
| I-121 | ((1S,2S,4R)-2-hydroxy-4-{[8-(1,2,3,4-tetrahydronaphthalen-1-yl)-9H-purin-6-yl]amino}cyclopentyl)methyl sulfamate; |
| I-122 | [(1S,2S,4R)-2-hydroxy-4-({8-[2-(trifluoromethyl)phenyl]-9H-purin-6-yl}amino)cyclopentyl]methyl sulfamate; |
| I-124 | {(1S,2S,4R)-4-[(6-{[(1S)-3,3-dimethyl-2,3-dihydro-1H-inden-1-yl]amino}pyrimidin-4-yl)oxy]-2-hydroxycyclopentyl}methyl sulfamate; |
| I-125 | {(1S,2S,4R)-2-hydroxy-4-[(4-{[(1R,2S)-2-methoxy-2,3-dihydro-1H-inden-1-yl]amino}-1,3,5-triazin-2-yl)amino]cyclopentyl}methyl sulfamate; |
| I-126 | ((1S,2S,4R)-2-hydroxy-4-{[8-(5,6,7,8-tetrahydronaphthalen-1-yl)-9H-purin-6-yl]amino}cyclopentyl)methyl sulfamate; |
| I-128 | {(1S,2S,4R)-4-[(8-cyclohexyl-9H-purin-6-yl)amino]-2-hydroxycyclopentyl}methyl sulfamate; |
| I-129 | ((1S,2S,4R)-4-{[8-(1-benzyl-1H-pyrazol-4-yl)-7H-purin-6-yl]oxy}-2-hydroxycyclopentyl)methyl sulfamate; |
| I-130 | {(1S,2S,4R)-2-hydroxy-4-[(9-methyl-8-phenyl-9H-purin-6-yl)amino]cyclopentyl}methyl sulfamate; |
| I-131 | {(1S,2S,4R)-2-hydroxy-4-[(8-tert-butyl-9H-purin-6-yl)amino]-2-hydroxycyclopentyl}methyl sulfamate; |
| I-133 | ((1S,2S,4R)-2-hydroxy-4-{[8-(2-methoxyphenyl)-9H-purin-6-yl]amino}cyclopentyl)methyl sulfamate; |
| I-134 | {(1S,2S,4R)-2-hydroxy-4-[(4-{[(1S)-3,3-dimethyl-2,3-dihydro-1H-inden-1-yl]amino}-1,3,5-triazin-2-yl)amino]-2-hydroxycyclopentyl}methyl sulfamate; |
| I-136 | [(1S,2S,4R)-2-hydroxy-4-({8-[(3-methylphenyl)sulfanyl]-7H-purin-6-yl}oxy)cyclopentyl]methyl sulfamate; |
| I-137 | [(1S,2S,4R)-4-({8-[2-(dimethylamino)phenyl]-9H-purin-6-yl}amino)-2-hydroxycyclopentyl]methyl sulfamate; |
| I-139 | ((1S,2S,4R)-2-hydroxy-4-{[8-(4-pyrrolidin-1-yl-1-naphthyl)-7H-purin-6-yl]oxy}cyclopentyl)methyl sulfamate; |
| I-140 | ((1S,2S,4R)-2-hydroxy-4-{[8-(1H-indol-3-yl)-7H-purin-6-yl]oxy}cyclopentyl)methyl sulfamate; |
| I-142 | {(1S,2S,4R)-2-hydroxy-4-[(6-{[(1R,2S)-2-methoxy-1,2,3,4-tetrahydronaphthalen-1-yl]amino}pyrimidin-4-yl)oxy]cyclopentyl}methyl sulfamate; |
| I-143 | {(1S,2S,4R)-2-hydroxy-4-[(6-{[(1S,2R)-2-methoxy-1,2,3,4-tetrahydronaphthalen-1-yl]amino}pyrimidin-4-yl)oxy]cyclopentyl}methyl sulfamate; |
| I-146 | ((1S,2S,4R)-4-{4-[(1S)-2,3-dihydro-1H-inden-1-ylamino]-5,6-dihydro-7H-pyrrolo[2,3-d]pyrimidin-7-yl}-2-hydroxycyclopentyl)methyl sulfamate; |
| I-147 | {(1S,2S,4R)-4-[(4-{[(1R)-2,2-difluoro-2,3-dihydro-1H-inden-1-yl]amino}-1,3,5-triazin-2-yl)amino]-2-hydroxycyclopentyl}methyl sulfamate; |
| I-150 | {(1S,2S,4R)-2-hydroxy-4-[(6-{[(1R,2S)-2-methoxy-4,4-dimethyl-1,2,3,4-tetrahydronaphthalen-1-yl]amino}pyrimidin-4-yl)oxy]cyclopentyl}methyl sulfamate; |

TABLE 1-continued

| | |
|---|---|
| I-151 | {(1S,2S,4R)-2-hydroxy-4-[(6-{[(1S,2R)-2-methoxy-4,4-dimethyl-1,2,3,4-tetrahydronaphthalen-1-yl]amino}pyrimidin-4-yl)oxy]cyclopentyl}methyl sulfamate; and |
| I-153 | [(1S,2S,4R)-4-({4-[(1S)-2,3-dihydro-1H-inden-1-ylamino]-1,3,5-triazin-2-yl}amino)-2-hydroxycyclopentyl]methyl sulfamate. |

Claiborne et al. further report that the compounds in the following Table 2 exhibited $IC_{50}$ values greater than 500 nM and less than 10 μM in this NAE assay (Claiborne Example 137).

TABLE 2

| | |
|---|---|
| I-4 | [(1R,2R,3S,4R)-4-({2-[(cyclohexylmethyl)amino]pyrimidin-4-yl}amino)-2,3-dihydroxycyclopentyl]methyl sulfamate |
| I-7 | ((1R,2R,3S,4R)-4-{[2-(benzylamino)pyrimidin-4-yl]amino}-2,3-dihydroxycyclopentyl)-methyl sulfamate |
| I-16 | {(1R,2R,3S,4R)-2,3-dihydroxy-4-[(pyridin-3-ylcarbonyl)amino]cyclopentyl}methyl sulfamate |
| I-28 | [(1R,2R,3S,4R)-2,3-dihydroxy-4-(isonicotinoylamino)cyclopentyl]methyl sulfamate |
| I-33 | [(1S,2S,4S)-4-({6-[(1S)-2,3-dihydro-1H-inden-1-ylamino]pyrimidin-4-yl}methyl)-2-hydroxycyclopentyl]methyl sulfamate |
| I-35 | {(1S,2S,4R)-4-[(2-{[(1S)-5-chloro-3,3-dimethyl-2,3-dihydro-1H-inden-1-yl]amino}-pyridin-4-yl)oxy]-2-hydroxycyclopentyl}methyl sulfamate |
| I-36 | {(1S,2S,4R)-2-hydroxy-4-[(7-methyl-8-phenyl-7H-purin-6-yl)amino]cyclopentyl}methyl sulfamate |
| I-48 | {(1S,2S,4R)-4-[(8-biphenyl-2-yl-9H-purin-6-yl)amino]-2-hydroxycyclopentyl}methyl sulfamate |
| I-53 | ((1S,2S,4R)-4-{[6-({(1S,2R)-2-[(dimethylamino)methyl]-2,3-dihydro-1H-inden-1-yl}-amino)pyrimidin-4-yl]oxy}-2-hydroxycyclopentyl)methyl sulfamate |
| I-54 | [(1S,2S,4R)-4-({6-[(1S)-2,3-dihydro-1H-inden-1-ylamino]-2-oxo-2,3-dihydropyrimidin-4-yl}amino)-2-hydroxycyclopentyl]methyl sulfamate |
| I-66 | ((1S,2S,4R)-4-{[6-({(1S,2S)-2-[(dimethylamino)carbonyl]-2,3-dihydro-1H-inden-1-yl}-amino)pyrimidin-4-yl]oxy}-2-hydroxycyclopentyl)methyl sulfamate |
| I-77 | {(1S,2S,4R)-2-hydroxy-4-[(6-{[(1S,2R)-1-methoxy-2,3-dihydro-1H-inden-2-yl]oxy}-pyrimidin-4-yl)oxy]cyclopentyl}methyl sulfamate |
| I-79 | {(1S,2S,4R)-2-hydroxy-4-[(6-{[(1R,2S)-1-methoxy-2,3-dihydro-1H-inden-2-yl]oxy}-pyrimidin-4-yl)oxy]cyclopentyl}methyl sulfamate |
| I-80 | {(1S,2S,4R)-4-[(9-benzyl-9H-purin-6-yl)oxy]-2-hydroxycyclopentyl}methyl sulfamate |
| I-81 | ((1S,2S,4R)-2-hydroxy-4-{[6-(2-phenylethyl)pyrimidin-4-yl]amino}cyclopentyl)methyl sulfamate |
| I-86 | ((1R,2R,3S,4R)-2,3-dihydroxy-4-{[6-(2-phenylethyl)pyrimidin-4-yl]amino}cyclopentyl)-methyl sulfamate |
| I-92 | {(1R,2R,3S,4R)-4-[(6-{[(1S,2S)-2-(benzyloxy)cyclopentyl]amino}pyrimidin-4-yl)amino]-2,3-dihydroxycyclopentyl}methyl sulfamate |
| I-94 | [(1S,2S,4R)-4-({2-[(1S)-2,3-dihydro-1H-inden-1-ylamino]pyridin-4-yl}oxy)-2-hydroxycyclopentyl]methyl sulfamate |
| I-96 | {(1S,2S,4R)-2-hydroxy-4-[(6-{[(1R,2S)-2-methoxy-2,3-dihydro-1H-inden-1-yl]oxy}-pyrimidin-4-yl)oxy]cyclopentyl}methyl sulfamate |
| I-98 | {(1S,2S,4R)-2-hydroxy-4-[(6-{[(1S,2R)-2-methoxy-2,3-dihydro-1H-inden-1-yl]oxy}-pyrimidin-4-yl)oxy]cyclopentyl}methyl sulfamate |
| I-110 | (1S,2S,4R)-2-(hydroxymethyl)-4-{[8-(5,6,7,8-tetrahydronaphthalen-1-yl)-9H-purin-6-yl]-amino}cyclopentanol |
| I-113 | [(1R,2R,3S,4R)-4-({2-[(1S)-2,3-dihydro-1H-inden-1-ylamino]-5-fluoropyrimidin-4-yl}-amino)-2,3-dihydroxycyclopentyl]methyl sulfamate |
| I-114 | {(1S,2S,4R)-2-hydroxy-4-[(6-phenylpyrimidin-4-yl)oxy]cyclopentyl}methyl sulfamate |
| I-119 | ((1S,2S,4R)-2-hydroxy-4-{[6-(1-naphthylmethoxy)pyrimidin-4-yl]oxy}cyclopentyl)methyl sulfamate |
| I-120 | ((1S,2S,4R)-4-{[6-(1,3-dihydro-2H-isoindol-2-yl)pyrimidin-4-yl]oxy}-2-hydroxycyclopentyl)methyl sulfamate |
| I-123 | {(1S,2S,4R)-2-hydroxy-4-[methyl(9-methyl-8-phenyl-9H-purin-6-yl)amino]cyclopentyl}-methyl sulfamate |
| I-127 | ((1S,2S,4R)-4-{[6-(cyclopentylamino)pyrimidin-4-yl]oxy}-2-hydroxycyclopentyl)methyl sulfamate |
| I-132 | {(1S,2S,4R)-4-[(6-benzylpyrimidin-4-yl)oxy]-2-hydroxycyclopentyl}methyl sulfamate |
| I-138 | (1S,2S,4R)-4-{[8-(2,3-dihydro-1,4-benzodioxin-5-yl)-9H-purin-6-yl]amino}-2-(hydroxymethyl)cyclopentanol |
| I-141 | ((1S,2S,4R)-2-hydroxy-4-{[6-(2-naphthylmethoxy)pyrimidin-4-yl]oxy}cyclopentyl)methyl sulfamate |
| I-148 | {(1S,2S,4R)-4-[(6-{[(1S,2R)-2,7-dimethoxy-1,2,3,4-tetrahydronaphthalen-1-yl]amino}-pyrimidin-4-yl)oxy]-2-hydroxycyclopentyl}methyl sulfamate |
| I-149 | {(1S,2S,4R)-4-[(6-{[(1R,2S)-2,7-dimethoxy-1,2,3,4-tetrahydronaphthalen-1-yl]amino}-pyrimidin-4-yl)oxy]-2-hydroxycyclopentyl}methyl sulfamate |
| I-152 | ((1S,3S)-3-{[8-(1-naphthyl)-9H-purin-6-yl]oxy}cyclopentyl)methyl sulfamate |

Claiborne et al. also report that the compounds in the following Table 3 exhibited $IC_{50}$ values greater than 10 μM in this NAE assay (Claiborne Example 137).

TABLE 3

| | |
|---|---|
| I-13 | {(1R,2R,3S,4R)-4-[(6-amino-2-methylpyrimidin-4-yl)amino]-2,3-dihydroxycyclopentyl}-methyl sulfamate |
| I-20 | [(1R,2R,3S,4R)-4-({2-[benzyl(methyl)amino]pyrimidin-4-yl}amino)-2,3-dihydroxycyclopentyl]methyl sulfamate |
| I-22 | [(1R,2R,3S,4R)-4-({6-[benzyl(methyl)amino]pyrimidin-4-yl}amino)-2,3-dihydroxycyclopentyl]methyl sulfamate |
| I-23 | {(1R,2R,3S,4R)-2,3-dihydroxy-4-[(pyridin-2-ylcarbonyl)amino]cyclopentyl}methyl sulfamate |
| I-30 | ((1R,2R,3S,4R)-4-{[6-(benzylamino)-2-methylpyrimidin-4-yl]amino}-2,3-dihydroxycyclopentyl)methyl sulfamate |
| I-31 | [(1S,2S,4R)-4-({6-[(1S)-2,3-Dihydro-1H-inden-1-ylamino]pyrimidin-4-yl}oxy)-2-hydroxycyclopentyl]methyl sulfamate |
| I-58 | [(1R,3R,4R)-3-({6-[(1S)-2,3-dihydro-1H-inden-1-ylamino]pyrimidin-4-yl}amino)-4-hydroxycyclopentyl]methyl sulfamate |
| I-61 | ((1S,2S,4R)-4-{[6-(3,4-dihydroisoquinolin-2(1H)-yl)pyrimidin-4-yl]oxy}-2-hydroxycyclopentyl)methyl sulfamate |
| I-76 | [(1S,3R,4R)-3-({6-[(1S)-2,3-dihydro-1H-inden-1-ylamino]pyrimidin-4-yl}amino)-4-hydroxycyclopentyl]methyl sulfamate |
| I-85 | {(1R,2R,3S,4R)-4-[(6-{[(1R,2R)-2-(benzyloxy)cyclopentyl]amino}pyrimidin-4-yl)amino]-2,3-dihydroxycyclopentyl}methyl sulfamate |
| I-89 | [(1S,2S,4R)-4-({6-[(4-chlorobenzyl)oxy]pyrimidin-4-yl}oxy)-2-hydroxycyclopentyl]methyl sulfamate |
| I-97 | [(1S,2S,4R)-2-hydroxy-4-(pyrimidin-4-yloxy)cyclopentyl]methyl sulfamate |
| I-144 | {(1R,2R,3S,4R)-4-[(2-{[(1S)-2,3-dihydro-1H-inden-1-ylamino]carbonyl}pyridin-4-yl)-amino]-2,3-dihydroxycyclopentyl}methyl sulfamate |
| I-145 | ((1R,2R,3S,4R)-4-{[2-(2,3-dihydro-1H-indol-1-ylcarbonyl)pyridin-4-yl]amino}-2,3-dihydroxycyclopentyl)methyl sulfamate |

Claiborne et al. also report sumo-activating enzyme (SAE) and ubiquitin-activating enzyme (UAE) HTRF assays in Example 137. However, no $IC_{50}$ values are reported.

Figure 1:
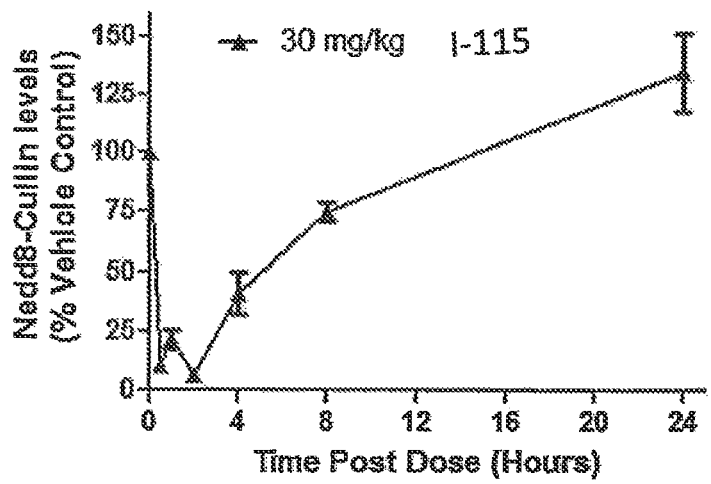
FIG. 1 shows the pharmacodynamic and pharmcokinetic parameters for {(1S,2S,4R)-2-hydroxy-4-[(6-{[(1R,2S)-2-meth oxy-2,3-dihydro-1H-inden-1-yl]amino}pyrimidin-4-yl)oxy]cyclopentyl}methyl sulfamate (I-115) in female Ncr nude mice bearing HCT116 tumor xenografts following a single subcutaneous administration at 30 mg/kg.
Figure 2:
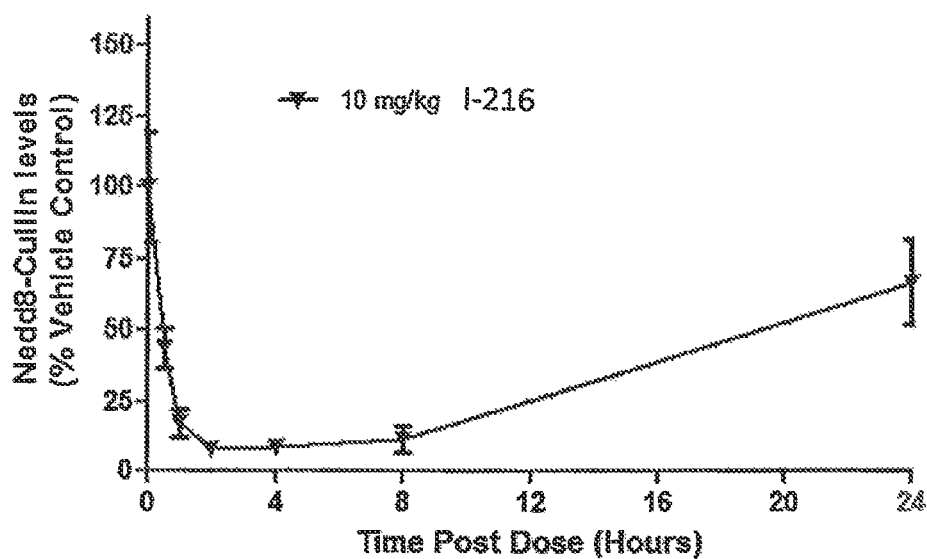

As shown in the Figures, the plasma AUC for I-216 administered at 10 mg/kg (FIG. 1) is comparable to that observed for I-115 administered at 30 mg/kg (FIG. 2), and approximately half the AUC observed for I-216 administered at 30 mg/kg (FIG. 3). Thus, compound I-216 is expected to be a 2- to 3-fold more potent inhibitor of NAE than I-115.

The term "about" is used herein to mean approximately, in the region of, roughly, or around. When the term "about" is used in conjunction with a numerical range, it modifies that range by extending the boundaries above and below the numerical values set forth. Unless otherwise specified, the term "about" is used herein to modify a numerical value above and below the stated value by a variance of 10%.

Unless otherwise specified, the terms "include" and "including" and the like are intended to be non-limiting. For example, "including" means including but not limited to, unless otherwise indicated.

In the compounds described herein, where relative stereochemistry is defined, the diastereomeric purity of the compound preferably is at least 80%, more preferably at least 90%, still more preferably at least 95%, and most preferably at least 99%. As used herein, the term "diastereomeric purity" refers to the amount of a compound having the depicted relative stereochemistry, expressed as a percentage of the total amount of all diastereomers present.

Preferably, the enantiomeric purity of the compound is at least 80%, more preferably at least 90%, still more preferably at least 95%, and most preferably at least 99%. As used herein, the term "enantiomeric purity" refers to the amount of a compound having the depicted absolute stereochemistry, expressed as a percentage of the total amount of the depicted compound and its enantiomer.

Methods for determining diastereomeric and enantiomeric purity are well-known in the art. Diastereomeric purity can be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity can be determined by any analytical method capable of quantitatively distinguishing between a compound and its enantiomer. Examples of suitable analytical methods include, without limitation, GC or HPLC, using a chiral column packing material. Enantiomers may also be distinguishable by NMR if first derivatized with an optically enriched derivatizing agent, e.g., Mosher's acid.

As used herein, "crystalline" refers to a solid in which the constituent atoms, molecules, or ions are packed in a regularly ordered, repeating three-dimensional pattern having a highly regular chemical structure. In particular, a crystalline salt may be produced as one or more crystalline forms. For the purposes of this application, the terms "crystalline form" and "polymorph" are synonymous; the terms distinguish between crystals that have different properties (e.g., different XRPD patterns, different DSC scan results). Pseudopolymorphs are typically different solvates of a material, and thus their properties differ from one another. Thus, each distinct polymorph and pseudopolymorph is considered to be a distinct crystalline form herein.

"Substantially crystalline" refers to salts that are at least a particular weight percent crystalline. Particular weight percentages include 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to salts that are at least 70% crystalline. In some embodiments, substantially crystalline refers to salts that are at least 80% crystalline. In some embodiments, substantially crystalline refers to salts that are at least 85% crystalline. In some embodiments, substantially crystalline refers to salts that are at least 90% crystalline. In some embodiments, substantially crystalline refers to salts that are at least 95% crystalline.

The term "solvate or solvated" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, hydrates, ethanolates, and methanolates.

The term "hydrate" refers to a solvate wherein the solvent molecule is $H_2O$ that is present in a defined stoichiometric amount, and includes, for example, hemihydrates, monohydrates, dihydrates, and trihydrates.

The term "mixture" refers to the combined components of the mixture regardless of the phase-state of the combination (e.g., liquid or liquid/crystalline).

The term "seeding" refers to the addition of crystalline material to a solution or mixture to initiate crystallization.

Some embodiments of the invention are directed to the I-216 hydrochloride salt, wherein at least a particular percentage by weight of the hydrochloride salt is crystalline. In some embodiments, the hydrochloride salt is substantially crystalline. Examples of a crystalline or substantially crystalline hydrochloride salt include a crystalline form of the hydrochloride salt or a mixture of different crystalline forms. Some embodiments of the invention are directed to a hydrochloride salt, wherein at least a particular percentage by weight of the hydrochloride salt is crystalline. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of the hydrochloride salt is crystalline, the remainder of the hydrochloride salt is the amorphous form of the hydrochloride salt.

Some embodiments of the invention are directed to the I-216 hydrochloride salt being a crystalline form, or being substantially a crystalline form. The crystalline form may be a particular percentage by weight of the crystalline hydrochloride salt. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of the hydrochloride salt is a designated crystalline form, the remainder of the hydrochloride salt is some combination of the amorphous form of the hydrochloride salt, and one or more crystalline forms of the hydrochloride salt excluding the designated crystalline form. In some embodiments, the hydrochloride salt is at least 90% by weight of a crystalline form. In some embodiments, the hydrochloride salt is at least 95% by weight of a crystalline form. In some embodiments, the hydrochloride salt is at least 80% by weight of a crystalline form. In some embodiments, the hydrochloride salt is at least 85% by weight of a crystalline form.

Unless otherwise specified, when a crystalline form of the hydrochloride salt is identified using one or more XRPD peaks given as angles 2θ, each of the 2θ values is understood to mean the given value ±0.2 degrees.

Throughout the specification and claims, when a crystalline form of the hydrochloride salt is identified using one or more temperatures from a DSC profile (e.g., onset of endothermic transition, melt, etc.), each of the temperature values is understood to mean the given value ±2° C.

Solid State Forms

Provided herein is an assortment of characterizing information to describe crystalline form 1 (Form 1) of the hydrochloride salt of I-216.

FIG. 4 shows an X-ray powder diffraction (XRPD) pattern of Form I of the hydrochloride salt of I-218 obtained using CuKα radiation. Peaks identified in FIG. 4 include those listed in Table 4.

TABLE 4

| Angle 2-Theta ° | Intensity % |
| --- | --- |
| 4.491 | 63.1 |
| 7.506 | 58.9 |
| 8.89 | 24.7 |
| 9.847 | 41.6 |
| 13.274 | 29.2 |
| 14.418 | 59.1 |
| 14.613 | 58 |
| 15.176 | 100 |
| 15.874 | 58.1 |
| 17.012 | 16.7 |
| 17.205 | 42.1 |
| 17.847 | 28.4 |
| 18.241 | 32.2 |
| 18.49 | 21.7 |
| 19.177 | 33.9 |
| 19.454 | 53.6 |
| 20.045 | 35.4 |
| 21.31 | 67.6 |
| 21.771 | 83.5 |
| 22.206 | 34.2 |
| 22.35 | 55.6 |
| 22.707 | 58.9 |
| 23.045 | 27.4 |
| 23.528 | 34.4 |
| 24.032 | 69.3 |
| 24.803 | 53.6 |
| 25.654 | 41.1 |
| 26.407 | 40.9 |
| 26.694 | 34.5 |
| 26.932 | 33.1 |
| 27.978 | 17 |
| 28.36 | 16.7 |
| 29.066 | 21.4 |

In some embodiments, Form I is characterized by an XRPD pattern having peaks at 2θ angles of 4.5°, 15.2°, 21.3°, 21.8° and 24.0°. In some embodiments, Form I is characterized by an XRPD pattern having peaks at 2θ angles of 4.5°, 7.5°, 14.4°, 14.6°, 15.2°, 15.9°, 19.5°, 21.3°, 21.8°, 22.4°, 22.7°, 24.0° and 24.8°. In some embodiments, Form I is characterized by an XRPD pattern having peaks at 2θ angles of 4.5°, 7.5°, 8.9°, 9.8°, 13.3°, 14.4°, 14.6°, 15.2°, 15.9°, 17.2°, 19.5°, 20.0°, 21.3°, 21.8°, 22.4°, 22.7°, 24.0°, 24.8°, 25.7° and 26.4°. In some embodiments, Form I is characterized by an XRPD pattern substantially as shown in FIG. 4.

In some embodiments, Form I is characterized by an XRPD pattern having a reference peak with a 2θ angle of 4.5±0.3°, and having peaks at 2θ angles of 10.7°, 16.8°, 17.3° and 19.5° relative to the reference peak. The term "reference peak" refers to a peak in the XRPD diffractogram that one skilled in the art considers as informing the polymorphic form of the material, i.e., differentiated from instrument noise. By "relative" it is meant that the observed 2θ angle of each peak will be the sum of the 2θ angle of the reference peak and the relative 2θ angle of that peak. For example, if the reference peak has a 2θ angle of 4.4°, the relative peaks will have 2θ angles of 15.1°, 21.2°, 21.7° and 23.9°; if the reference peak has a 2θ angle of 4.5°, the relative peaks will have 2θ angles of 15.2°, 21.3°, 21.8° and 24.0°; if the reference peak has a 2θ angle of 4.6°, the relative peaks will have 2θ angles of 15.3°, 21.4°, 21.9° and 24.1°; etc. In some embodiments, Form I is characterized by an XRPD pattern having a reference peak with a 2θ angle of 4.5±0.3°, and having peaks at 2θ angles of 3.0°, 9.9°, 10.1°, 10.7°, 11.4°, 15.0°, 16.8°, 17.3°, 17.9°, 18.2°, 19.5° and 20.3° relative to the reference peak. In some embodiments, Form I is characterized by an XRPD pattern having a reference peak with a 2θ angle of 4.5±0.3°, and having peaks at 2θ angles of 3.0°, 4.4°, 5.3°, 8.8°, 9.9°, 10.1°, 10.7°, 11.4°, 12.7°, 15.0°, 15.5°, 16.8°, 17.3°, 17.9°, 18.2°, 19.5°, 20.3°, 21.2° and 21.9° relative to the reference peak. Any of the peaks that one skilled in the art considers as informing the polymorphic form of the material can serve as the reference peak and the relative peaks can then be calculated. For example, if the reference peak has a 2θ angle of 24.0°, then the relative peaks will have 2θ angles of −19.5°, −8.8°, −2.7° and −2.2° relative to the reference peak. FIG. 5 shows a differential scanning calorimetry (DSC) profile of Form I. The DSC thermogram plots the heat flow as a function of temperature from a sample, the temperature rate change being about 10° C./min. In some embodiments, Form I is characterized by a DSC profile substantially as shown in FIG. 5. FIG. 5 shows an endotherm event with onset of about 129.8° C. and peak at about 135.6° C. corresponding to the loss of water coupled with melting. A broad endotherm with an onset of about 181.6° C. and peak at about 195.5° C., and a sharp endotherm with an onset of about 275.3° C. and peak at about 275.5° C. are also observed.

FIG. 6 shows a thermal gravimetric analysis (TGA) profile of Form I of the hydrochloride salt of I-216. The TGA thermogram plots the percent loss of weight of the sample as a function of temperature, the temperature rate change being about 10° C./min. FIG. 6 shows approximately 3.7% weight loss between 100° C. to 150° C., suggesting that I-216 HCl Form I is a monohydrate. In some embodiments, I-216 HCl Form I is characterized by a TGA profile substantially as shown in FIG. 6. Karl Fischer measurements show a water content of about 3.5%, further suggesting that the loss of weight seen in the TGA profile is due to the loss of water, indicating Form I is a monohydrate.

FIG. 10 shows an X-ray powder diffraction (XRPD) pattern of Form II of the hydrochloride salt of I-216 obtained using CuKα radiation. Peaks identified in FIG. 10 include those listed in Table 5.

TABLE 5

| Angle 2-Theta ° | Intensity % |
| --- | --- |
| 3.261 | 8.4 |
| 4.269 | 24.9 |
| 6.85 | 5.1 |
| 8.693 | 81.3 |
| 11.1 | 2.6 |
| 11.252 | 3.8 |
| 12.426 | 18.4 |
| 13.115 | 3.3 |
| 13.522 | 3.6 |
| 14.529 | 13 |
| 15.176 | 37.4 |
| 15.708 | 100 |
| 16.574 | 6.9 |
| 17.253 | 11.3 |
| 18.202 | 12 |
| 18.495 | 11.8 |
| 19.579 | 37.2 |
| 20.014 | 27.6 |
| 20.813 | 20.1 |
| 22.004 | 18.4 |
| 22.456 | 23 |
| 23.128 | 29 |
| 24.234 | 50.4 |
| 24.728 | 18 |
| 25.737 | 16.5 |
| 28.163 | 9.6 |
| 29.403 | 11 |

In some embodiments, Form II is characterized by an XRPD pattern having peaks at 2θ angles of 8.7°, 15.2°, 15.7°, 19.6° and 24.2°. In some embodiments, Form II is characterized by an XRPD pattern having peaks at 2θ angles of 4.3°, 8.7°, 15.2°, 15.7°, 19.6°, 20.0°, 20.8°, 22.5°, 23.1° and 24.2°. In some embodiments, Form II is characterized by an XRPD pattern having peaks at 2θ angles of 4.3°, 8.7°, 12.4°, 14.5°, 15.2°, 15.7°, 17.3°, 18.2°, 18.5°, 19.6°, 20.0°, 20.8°, 22.0°, 22.5°, 23.1°, 24.2°, 24.7°, 25.7°, 28.2° and 29.4°. In some embodiments, Form II is characterized by an XRPD pattern substantially as shown in FIG. 10.

In some embodiments, Form II is characterized by an XRPD pattern having a reference peak with a 2θ angle of 8.7±0.3°, and having peaks at 2θ angles of 6.5°, 7.0°, 10.9° and 15.5° relative to the reference peak. The terms "reference peak" and "relative" have the same meaning as previously described. In some embodiments, Form II is characterized by an XRPD pattern having a reference peak with a 2θ angle of 8.7±0.3°, and having peaks at 2θ angles of −4.4°, 6.5°, 7.0°, 10.9°, 11.3°, 12.1°, 13.8°, 14.4°, and 15.5°, relative to the reference peak. In some embodiments, Form II is characterized by an XRPD pattern having a reference peak with a 2θ angle of 8.7±0.3°, and having peaks at 2θ angles of −4.4°, 3.7°, 5.8°, 6.5°, 7.0°, 8.6°, 9.5°, 9.8°, 10.9°, 11.3°, 13.3°, 13.8°, 14.4°, 15.5°, 16.0°, 17.0°, 19.5° and 20.7° relative to the reference peak. Any of the peaks that one skilled in the art considers as informing the polymorphic form of the material can serve as the reference peak and the relative peaks can then be calculated. For example, if the reference peak has a 2θ angle of 24.2°, then the relative peaks will have 2θ angles of −15.5°, −9.0°, −8.5° and −4.6° relative to the reference peak.

Synthetic Methods

Compound I-216 can be prepared by methods known to one skilled in the art and/or by reference to the schemes shown below and the examples that follow. Exemplary synthetic routes are set forth in Schemes 1-4 below, and in the Examples below.

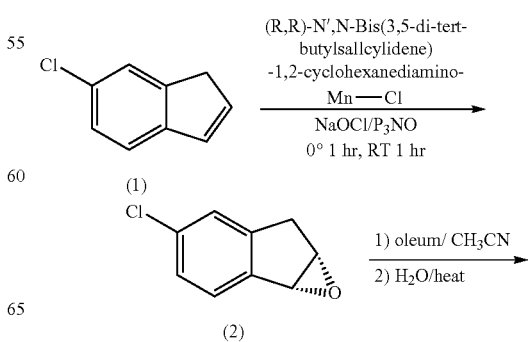

Scheme 1

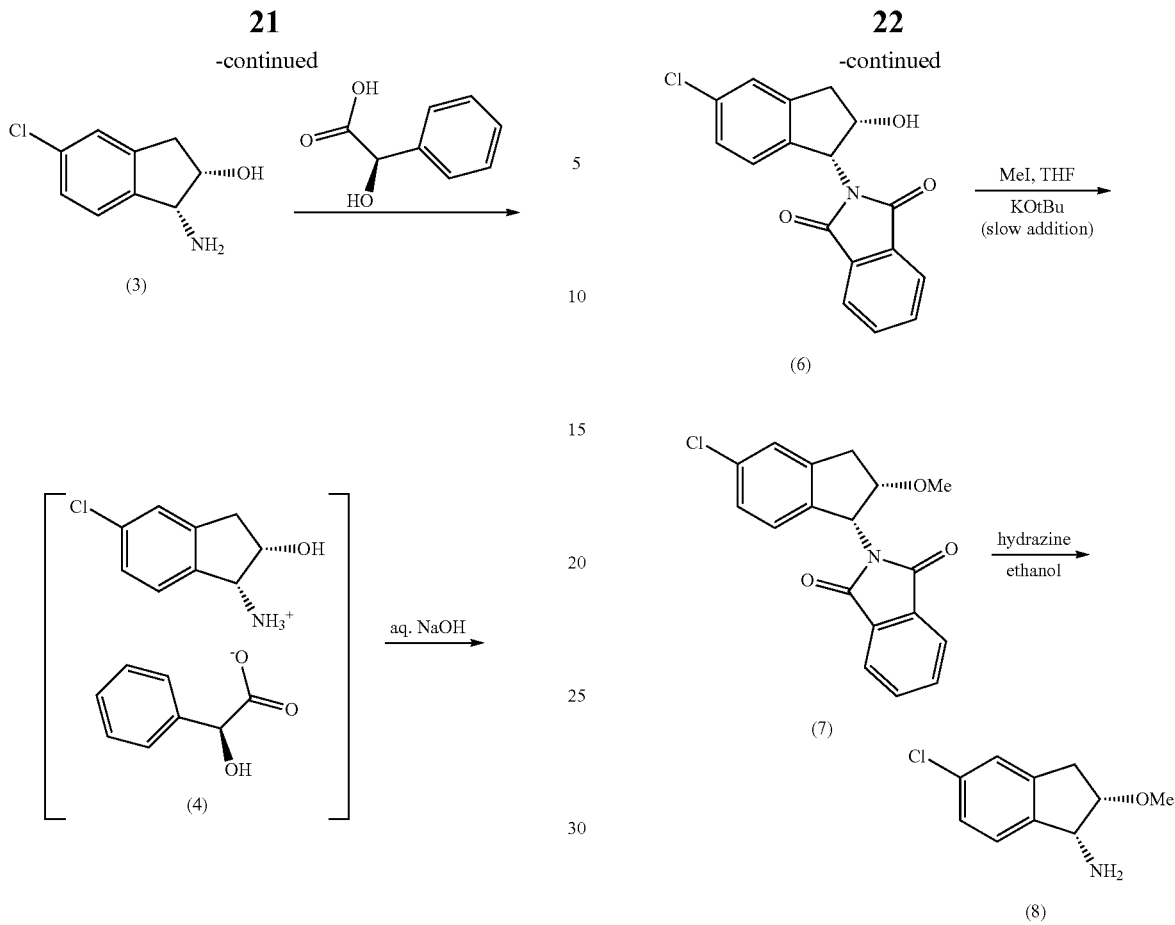

Scheme 1 describes the synthesis of (1R,2S)-5-chloro-2-methoxyindan-1-amine (8) which is further exemplified in Example 1 below. 6-chloro-1H-indene (1) was epoxidized using the Jacobsen catalyst to give oxirene (2) which was treated with fuming sulfuric acid in acetonitrile which led, after the addition of water and heating to rel-(1R,2S)-1-amino-5-chloroindan-2-ol (3). Rel-(1R,2S)-1-amino-5-chloroindan-2-ol (3) was chirally resolved using D-(−)-mandelic acid to give (1R,2S)-1-amino-5-chloroindan-2-ol (5) after removal of the chiral auxiliary. Protection of the primary amine in (5) was achieved using phthalic anhydride leading to compound (6). Methylation of the hydroxyl group with methyl iodide lead to compound (7), which was subsequently deprotected with hydrazine to give the desired (1R,2S)-5-chloro-2-methoxyindan-1-amine (8).

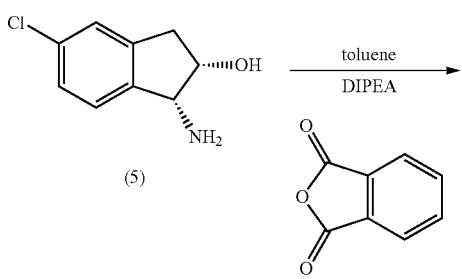

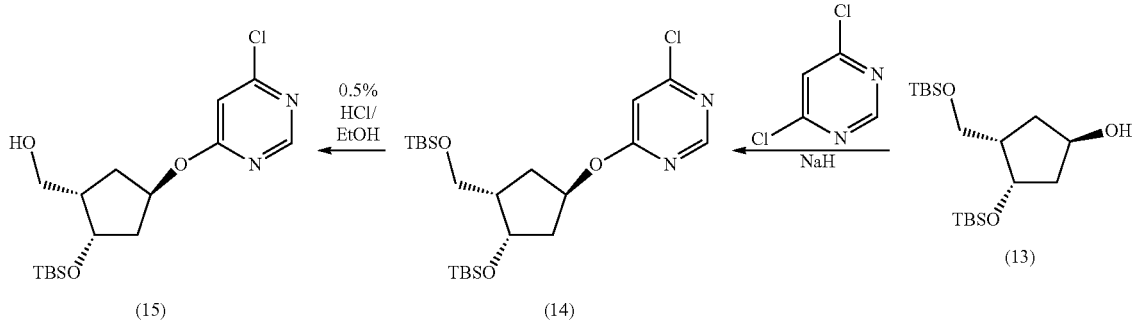

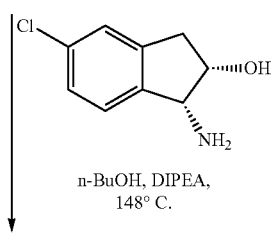

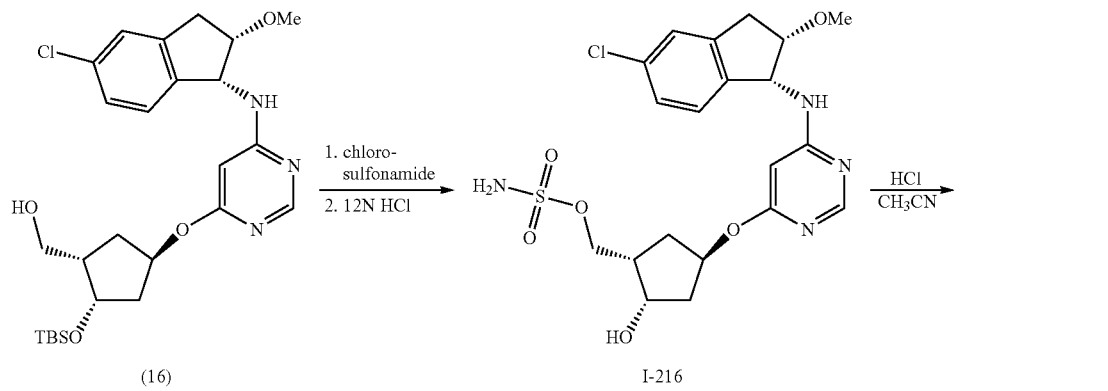

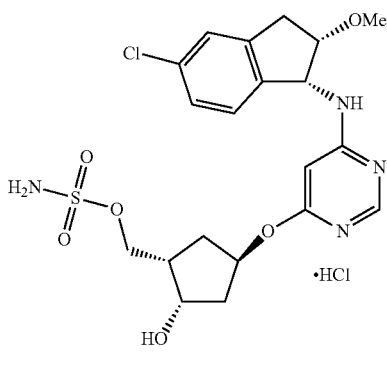

Scheme 2 shows the synthesis of {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate HCl Form 1 which is further exemplified in Example 2 below. The primary alcohol of racemic-(9) was protected as the tert-butyldimethylsilyl ether to give compound (10) which was enzymatically resolved using *Candida Antartica* on acrylic resin to give compound (11) with an enantiomeric excess of greater than 99%. The secondary alcohol in (11) was then protected as its tart-butyldimethylsilyl ether to afford (12). Compound (12) was treated with catechol borane in the presence of Wilkinson's catalyst to afford (13) which was further reacted with 4,6-dichloropyrimidine to afford compound (14). The primary alcohol of (14) was selectively deprotected and then the indane portion of the molecule was installed by reaction of (15) with (1R,2S)-5-chloro-2-methoxyindan-1-amine (8) to afford compound (16). I-216 was prepared by reacting compound

(16) with chlorosulfonamide, followed by deprotection of the secondary alcohol under acidic conditions. I-216 was treated with hydrochloric acid in acetonitrile to afford Form I of the hydrochloride salt of I-216.

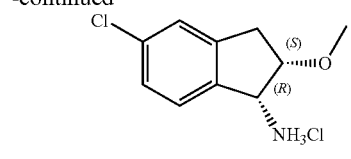

(20)

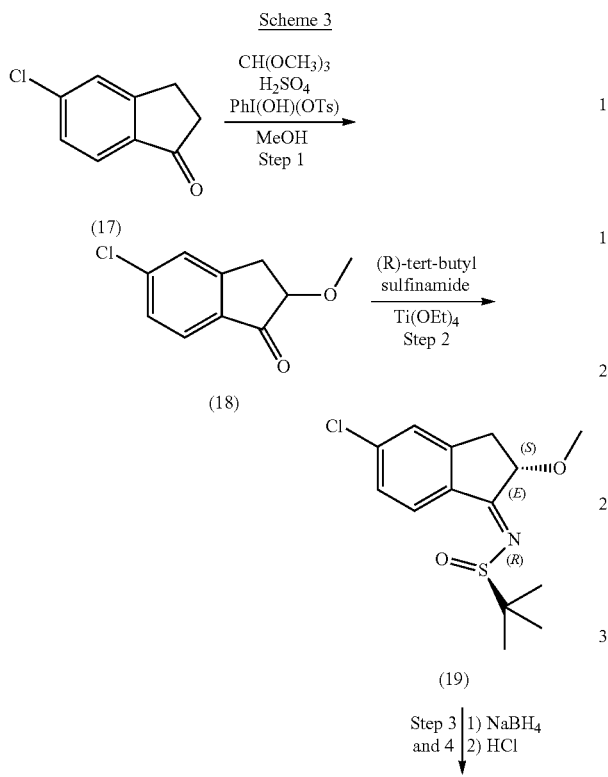

Scheme 3 describes the preparation of (1R,2S)-5-chloro-2-methoxy-2,3-dihydro-1H-inden-1-amine hydrochloride (20) which is further exemplified in Example 4 below. 5-chloro-2,3-dihydro-1H-inden-1-one (17) was reacted with trimethylorthoformate under acidic conditions, followed by treatment with Koser's reagent [PhI(OH)(OTs)] to give 5-chloro-2-methoxy-2,3-dihydro-1H-inden-1-one (18). The indenone was treated with (R)-tert-butyl sulfinamide in the presence of titanium tetraethoxide to afford the corresponding sulfinamide (19). The reaction was allowed to proceed until less than 5% of the undesired diastereoisomer could be detected by HPLC. The crude sulfinamide was reduced using NaBH$_4$ to afford the primary amine which was treated with hydrochloric acid to afford (1R,2S)-5-chloro-2-methoxy-2,3-dihydro-1H-inden-1-amine hydrochloride (20).

-continued

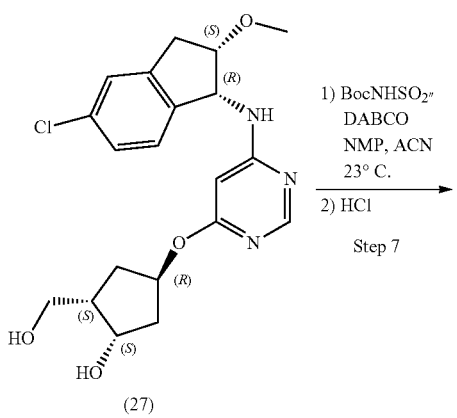

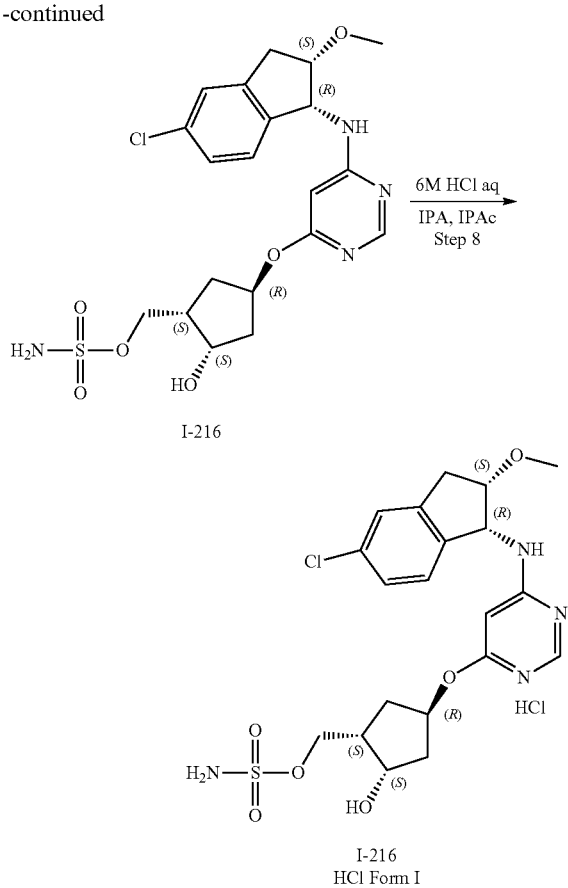

I-216 HCl Form I

Scheme 4 shows a route for the preparation of I-216 hydrochloride salt Form I which is further exemplified in Example 5 below. The epoxide in (1S,2R,3S,5R)-3-(benzyloxy)-2-(benzyloxymethyl)-6-oxabicyclo[3.1.0]hexane (21) was ring opened by treatment with lithium diisopropylamide and the resulting anion was trapped by treatment with trimethylsilylchloride to afford (22). The double bond was reduced using hydrogen and a Pd/BaSO$_4$ catalyst and the trimethylsilyl protecting group was removed to afford secondary alcohol (23). Secondary alcohol (23) was mesylated and then treated with tetrabutylammonium acetate followed by sodium hydroxide to afford (24) which was reacted with sodium hydride and 4,6-dichloropyrimidine to afford intermediate (25). Removal of the benzyl protecting groups using boron trichloride to afford (26) followed by reaction with (1R,2S)-5-chloro-2-methoxy-2,3-dihydro-1H-inden-1-amine hydrochloride (20) at 130° C. and 50 psi led to the formation of ((1S,2S,4R)-4-(6-((1R,2S)-5-chloro-2-methoxy-2,3-dihydro-1H-inden-1-ylamino)pyrimidin-4-yloxy)-2-hydroxycyclopentyl)methyl sulfamate (27). The primary alcohol in compound (27) was sulfamated to afford I-216. Form I of the hydrochloride salt of I-216 was generated by treatment of I-216 in isopropyl alcohol with 6M hydrochloric acid followed by addition of isopropyl acetate as an anti-solvent.

Uses

The chemical entities of this invention are useful inhibitors of E1 enzyme activity. In particular, the chemical entities are designed to be inhibitors of NAE. Inhibitors are meant to include chemical entities which reduce the promoting effects of E1 enzymes in ubl (in particular, Nedd8) conjugation to target proteins (e.g., reduction of ubiquitination, neddylation), reduce intracellular signaling mediated by ubl (in particular, Nedd8) conjugation, and/or reduce proteolysis mediated by ubl (in particular, Nedd8) conjugation (e.g., inhibition of cullin-dependent ubiquitination and proteolysis (e.g., the ubiquitin-proteasome pathway)). Thus, the chemical entities of this invention may be assayed for their ability to inhibit the E1 enzyme in vitro or in vivo, or in cells or animal models according to methods provided in further detail herein, or methods known in the art. The chemical entities may be assessed for their ability to bind or mediate E1 enzyme activity directly. Alternatively, the activity of the chemical entities may be assessed through indirect cellular assays, or assays measuring downstream effects of E1 activation to assess inhibition of downstream effects of E1 inhibition (e.g., inhibition of cullin-dependent ubiquitination and proteolysis). For example, activity may be assessed by detection of ubl-conjugated substrates (e.g., ubl-conjugated E2s, neddylated cullins, ubiquitinated substrates); detection of downstream protein substrate stabilization (e.g., stabilization of p27, stabilization of IκB); detection of inhibition of UPP activity; detection of downstream effects of protein E1 inhibition and substrate stabilization (e.g., reporter assays, e.g., NFκB reporter assays, p27 reporter assays). Assays for assessing activities are described below in the Experimental section and/or are known in the art.

It will be appreciated that the chemical entities of this invention may be derivatized at functional groups to provide prodrug derivatives which are capable of conversion back to the parent chemical entities in vivo. Examples of such prodrugs include the physiologically acceptable and metabolically labile derivatives. More specifically, the prodrug of the chemical entity of this invention is a carbamate or amide of the —NH— group of the chemical entity, or an ether or ester of the —OH group of the chemical entity.

Such carbamate prodrugs of the —NH— group of the chemical entity include the following carbamates: 9-fluorenylmethyl, 9-(2-sulfo)fluorenylmethyl, 9-(2,7-dibromo) fluorenylmethyl, 17-tetrabenzo[a,c,g,i]fluorenylmethyl, 2-chloro-3-indenylmethyl, benz[f]inden-3-ylmethyl, 2,7,di-tert-butyl-[9-(10,10-dioxo-10,10,10,10-tetrahydrothioxanthyl)]methyl, 1,1-dioxobenzo[b]thiophene-2-yl-methyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'- and 4'-pyridyl)ethyl, 2,2-bis(4'-nitrophenyl)ethyl, N-2-pivaloylamino)-1,1-dimethylethyl, 2-[(2-nitrophenyl)dithio]-1-phenylethyl, 2-(N,N-dicyclohexylcarboxamideo)ethyl, tert-butyl, 1-adamantyl, 2-adamantyl, vinyl, allyl, 1-isopropylallyl, cinnamyl, 4-nitrocinnamyl, 3-(3'-pyridyl)prop-2-enyl, 8-quinolyl, N-hydroxypiperidinyl, alkyldithio, benzyl, para-methoxybenzyl, para-nitrobenzyl, para-bromobenzyl, para-chlorobenzyl, 2,4-dichlorobenzyl, 4-methylsulfinylbenzyl, 9-anthrylmethyl, diphenylmethyl, phenothiazinyl-(10)-carbonyl, N'-para-toluenesulfonylaminocarbonyl and N'-phenylaminothiocarbonyl.

Such amide prodrugs of the —NH— group of the chemical entity include the following amides: N-formyl, N-acetyl, N-chloroacetyl, N-trichloroacetyl, N-trifluoroacetyl, N-phenylacetyl, N-3-phenylpropionyl, N-4-pentenoyl, N-picolinoyl, N-3-pyridylcarboxamido, N-benzoylphenylalanyl, N-benzoyl and N-para-phenylbenzoyl.

Such ether prodrugs of the —OH group of the chemical entity include the following ethers: methyl, methoxymethyl, methylthiomethyl, (phenyldimethylsilyl)methoxymethyl, benzyloxymethyl, para-methoxybenzyloxymethyl, para-nitrobenzyloxymethyl, ortho-nitrobenzyloxymethyl, (4-methoxyphenoxy)methyl, guaiacolmethyl, tert-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, menthoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl, 2,3,3a,4,5,8,7,7a-octahydro-7,8,8,-trimethyl-4,7-methanobenzofuran-2-yl, 1-ethoxyethyl 1-(2-chloroethoxy)ethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2,-trichloroethyl, 1,1-dianisyl-2,2,2,-trichloroethyl, 1,1,1,3,3,3-hexafluoro-2-phenylisopropyl, 2-trimethylsilylethyl, 2-(benzylthio)ethyl, 2-(phenylselenyl)ethyl, tert-butyl, allyl, propargyl, para-chlorophenyl, para-methoxyphenyl, para-nitrophenyl, 2,4-dinitrophenyl, 2,3,5,8-tetrafluoro-4-trifluoromethyl)phenyl, benzyl, para-methoxybenzyl, 3,4-dimethoxybenzyl, ortho-nitrobenzyl, para-nitrobenzyl, para-halobenzyl, 2,6-dichlorobenzyl, para-cyanobenzyl, para-phenylbenzyl, 2,6-difluorobenzyl, para-acylaminobenzyl, para-azidobenzyl, 4-azido-3-chlorobenzyl, 2-trifluoromethylbenzyl, para-(methylsulfinyl) benzyl, 2-picolyl, 4-picolyl, 3-methyl-2-picolyl N-oxido, 2-quinolinylmethyl, 1-pyrenylmethyl, diphenylmethyl, p,p'-dinitrobertzhydryl, 5-dibenzosuberyl, triphenylmethyl, alpha-naphthyldiphenylmethyl, para-methoxyphenyldiphenylmethyl, di(para-methoxyphenyl)phenylmethyl, tri(para-methoxyphenyl)methyl, 4-(4'-bromophenacyloxy)phenyldiphenylmethyl, 4,4',4"-tris(4,5-dichlorophthalimidophenyl) methyl, 4,4',4"-tri(levulinoyloxyphenyl)methyl, 4,4',4"-tri(benzoyloxyphenyl)methyl, 4,4'-dimethoxy-3"-[N-(imidazolylmethyl)trityl, 4,4'-dimethoxy-3"[N-imidazolylethyl]carbamoyl]trityl, 1,1-bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl, triethylsilyl, triisopropylsilyl, dimethylisopropylsilyl, diethylisopropylsilyl, dimethylthexylsilyl, tert-butyldimethylsilyl, tert-butyldiphenylsilyl, tribenzylsilyl, tri-para-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl and tert-butoxydiphenylsilyl.

Such ester prodrugs of the —OH group of the chemical entity include the following esters: formate, benzoylformate, acetate, chloroacetate, dichloroacetate, trichloroacetate, trifluoroacetate, methoxyacetate, triphenylmethoxyacetate, phenoxyacetate, para-chlorophenoxyacetate, phenylacetate, para-P-phenylacetate, diphenylacetate, nicotinate, 3-phenylpropionate, 4-pentenoate, 4-oxopentanoate, 4,4-(ethylenedithio)pentanoate, 5-[3-bis(4-methoxyphenyl)hydroxymethylphenoxy]levulinate, pivaloate, 1-adamantoate, crotonate, 4-methoxycrotonate, benzoate, para-phenylbenzoate and 2,4,6-trimethylbenzoate. Additionally, any physiologically acceptable equivalents of the present chemical entities, similar to the metabolically labile ether, esters of the —OH group, or carbamates or amides of the —NH— group, which are capable of producing the parent chemical entities described herein in vivo, are within the scope of this invention. See e.g., Greene and Wuts, Protective Groups in Organic Synthesis, 3$^{rd}$ Ed. John Wiley & Sons, Inc. (1999).

Some embodiments of this invention relate to a composition comprising a chemical entity of this invention and a pharmaceutically acceptable carrier. Some embodiments of this invention relate to a composition comprising a prodrug of a chemical entity of this invention and a pharmaceutically acceptable carrier.

If a pharmaceutically acceptable salt is the chemical entity of the invention utilized in these compositions, the salts preferably are derived from inorganic or organic acids and bases. For reviews of suitable salts, see, e.g., Berge et al, *J. Pharm. Sol* 66:1-19 (1977) and *Remington: The Science and Practice of Pharmacy,* 20th Ed., A. Gennaro (ed.), Lippincott Williams & Wilkins (2000) ("Remington's").

Examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of the invention preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent. Many such pharmaceutically acceptable carriers are known in the art. See, e.g., *Remington's; Handbook of Pharmaceutical Excipients,* 6th Ed., R. C. Rowe et al. (eds.), Pharmaceutical Press (2009).

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. In such solid dosage forms, the active chemical entity is mixed with at least one inert, pharmaceutically acceptable excipient or carrier such as sodium citrate or dicalcium phosphate and/or a) fillers or extenders such as starches, lactose, sucrose, glucose, mannitol, micro-crystalline cellulose and silicic acid, b) binders such as, for example, carboxymethylcellulose, alginates, gelatin, sucrose, and acacia, c) humectants such as glycerol, d) disintegrating agents such as agar-agar, calcium carbonate, polyvinylpyrrolidinone, croscarmellose, sodium starch glycolate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, sodium stearyl fumarate, solid polyethylene glycols, sodium lauryl sulfate, silicon dioxide and mixtures thereof. In the case of capsules, tablets and pills, the dosage form may also comprise buffering agents.

The active chemical entity can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). The term "subject" as used herein, means an animal, preferably a mammal, more preferably a human. The term "patient" as used herein, means a human. Preferably, the composition is formulated for administration to a patient or subject having or at risk of developing or experiencing a recurrence of the relevant disorder being treated. Preferred pharmaceutical compositions of the invention are those formulated for oral, intravenous, or subcutaneous administration. However, any of the above dosage forms containing a therapeutically effective amount of a chemical entity of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

By "therapeutically effective amount" is meant an amount of the chemical entity or composition sufficient, upon single or multiple dose administration, to cause a detectable decrease in E1 enzyme activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of E1 enzyme inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific chemical entity employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In some embodiments, the invention relates to a method of inhibiting or decreasing E1 enzyme activity in a sample comprising contacting the sample with a chemical entity of this invention, or composition comprising a chemical entity of the invention. The sample, as used herein, includes sample comprising purified or partially purified E1 enzyme, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of E1 enzyme activity in a sample may be carried out in vitro or in vivo, in cellulo, or in situ.

In some embodiments, the invention provides a method for treating a patient having a disorder, a symptom of a disorder, at risk of developing, or experiencing a recurrence of a disorder, comprising administering to the patient a chemical entity or pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

Disease applications include those disorders in which inhibition of E1 enzyme activity is detrimental to survival and/or expansion of diseased cells or tissue (e.g., cells are sensitive to E1 inhibition; inhibition of E1 activity disrupts disease mechanisms; reduction of E1 activity stabilizes protein which are inhibitors of disease mechanisms; reduction of E1 activity results in inhibition of proteins which are activators of disease mechanisms). Disease applications are also intended to include any disorder, disease or condition which requires effective cullin and/or ubiquitination activity, which activity can be regulated by diminishing E1 enzyme activity (e.g., NAE activity).

For example, methods of the invention are useful in treatment of disorders involving cellular proliferation, including disorders which require an effective cullin-dependent ubiquitination and proteolysis pathway (e.g., the ubiquitin proteasome pathway) for maintenance and/or progression of the disease state. The methods of the invention are useful in treatment of disorders mediated via proteins (e.g., NFκB activation, p27$^{Kip}$ activation, p21$^{WAF/CIP1}$ activation, p53 activation) which are regulated by E1 activity (e.g., NAE activity). Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neuron disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), small cell lung cancer, bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer, and soft tissue sarcoma.

In some embodiments, the cancer is a hematologic malignancy. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

Depending on the particular disorder or condition to be treated, in some embodiments, the E1 enzyme inhibitor of the invention is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated."

The E1 inhibitor of the invention may be administered with the other therapeutic agent in a single dosage form or as a separate dosage form. When administered as a separate dosage form, the other therapeutic agent may be administered prior to, at the same time as, or following administration of the E1 inhibitor of the invention.

In some embodiments, the E1 enzyme inhibitor of the invention is administered in conjunction with a therapeutic agent selected from cytotoxic agents, radiotherapy, and immunotherapy appropriate for treatment of proliferative disorders and cancer. Examples of cytotoxic agents suitable for use in combination with the E1 enzyme inhibitors of the invention include: antimetabolites, including, e.g., capecitibine, gemcitabine, 5-fluorouracil or 5-fluorouracil/ leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; including, e.g., CC-5013 and CC-4047; protein tyrosine kinase inhibitors, including, e.g., imatinib mesylate and gefitinib; proteasome inhibitors, including, e.g., bortezomib; thalidomide and related analogs; antibodies, including, e.g., trastuzumab, rituximab, cetuximab, and bevacizumab; mitoxantrone; dexamethasone; prednisone; and temozolomide.

Other examples of agents the inhibitors of the invention may be combined with include anti-inflammatory agents such as corticosteroids, TNF blockers, Il-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

In order that this invention be more fully understood, the following preparative and testing examples are set forth. These examples are for the purpose of illustration only and are not intended to be construed as limiting the scope of the invention in any way.

EXAMPLES

Abbreviations

AcOH acetic acid
ACN acetonitrile
DABCO triethylenediamine
DCM dichloromethane
DCP 4,6-dichloropyrimidine
DEA diethylamine
DIPEA N,N-diisopropylethylamine
DMSO dimethylsulfoxide
Et$_2$O diethyl ether
EtOAc ethyl acetate
EtOH ethanol
Et$_3$N triethylamine
FA formic acid
H$_2$O water
h hours
IPA isopropyl alcohol
IPAc isopropyl acetate
LCMS liquid chromatography mass spectrum
LDA lithium diisopropylamide
MTBE methyl tert-butyl ether
MeOH methanol
min minutes
MS mass spectrum
NMP N-methyl-2-pyrrolidone
rt room temperature
P$_3$NO 4-phenylpropylpyridine-N-oxide
TBS tert-butyldimethylsilyl
TFA trifluoroacetic acid
THF tetrahydrofuran
TLC thin layer chromatography
TMS trimethylsilyl General Methods X-ray Powder Diffraction. XRPD was performed using a Bruker AXS D8 Advance X-ray Diffractometer. Approximately 100 mg sample was gently flattened into a 50 mm diameter quartz sampling pan for powder measurements. The sample was run as a continuous scan from 2.9 to 29.6 °2θ using 2θ/θ locked coupled angles. Each angle interval was 0.05 °2θ and the data were collected for 2 seconds. The sample run occurred under ambient conditions, and all data analysis was performed using EVA version 9.0 software.

Thermal Analysis. The thermal events were analyzed using differential scanning calorimetry (DSC) and thermogravimetric analysis (TGA). TA instruments DSC Q200 and TGA Q500 were used for all sample runs. The thermograms were analyzed using Thermal Advantage for Q Series software.

Differential Scanning calorimetry. The sample (I-2 mg) was sealed in an aluminum pan with lid. The sample was heated at a ramp rate of 10° C./min from 25° to 400° C., while the nitrogen sample purge was kept constant at 50 mL/min.

Thermogravimetric Analysis. The sample (5-10 mg) was run in an open platinum pan. The sample was heated at a ramp rate of 10° C./min to 400° C., with a nitrogen sample purge of 60 mL/min.

Example 1. Synthesis of (1R,2S)-5-chloro-2-methoxyindan-1-amine (8)

Step 1: rel-(1aR,6aS)-4-chloro-6,6a-dihydro-1aH-indeno[1,2-b]oxirene (2)

To a stirring solution of 4-phenylpropylpyridine-N-oxide (278 mg, 1.31 mmol) in methylene chloride (20 mL) was added (R,R)-Jacobsen catalyst (237.0 mg, 0.3732 mmol) and a solution of sodium hypochlorite (2.0 M in water; 16 mL, 32 mmol) at 0° C. The resulting brown suspension was stirred at 0° C. for 15 minutes then a solution of 6-chloro-1H-indene (1) (2.81 g, 18.6 mmol) in methylene chloride (20 mL) was added via syringe with simultaneous addition of additional sodium hypochlorite (2.0M in water; 16 mL, 32 mmol). The reaction was stirred at 0° C. for one hour then the ice bath was removed and the reaction was stirred at room temperature for 1 hr. An aliquot was taken and TLC on silica (hexanes) showed all starting material consumed. The reaction was poured into brine and extracted with methylene chloride. The combined extracts were washed with saline, then dried over sodium sulfate, filtered, and evaporated under reduced pressure to leave crude product which solidified when placed under hi-vacuum. Yield ~3.7 g of a brown solid. $^1$H NMR (400 MHz, DMSO) δ 7.55 (d, J=7.6 Hz, 1H), 7.32 (s, 1H), 7.23 (d, J=7.3 Hz, 1H), 4.36 (s, 1H), 4.16 (s, 1H), 3.03 (dd, J=45.8, 18.2 Hz, 2H).

Step 2: rel-(1R,2S)-1-amino-5-chloroindan-2-ol (3)

To a −40° C. mixture of fuming sulfuric acid (4.098 mL, 44.06 mmol) in acetonitrile (30 mL, 500 mmol) was added dropwise a suspension of rel-(1aR,6aS)-4-chloro-6,6a-dihydro-1aH-indeno[1,2-b]oxirene (2) (2.94 g, 17.6 mmol) in acetonitrile (70 mL) and hexane (40 mL). The biphasic mixture was then allowed to warm to room temperature and was stirred for an additional hour, leaving a hazy, rusty red colored mixture. Water (30 mL) was carefully added (all solids dissolved to give a reddish-brown solution) and the resulting solution was stirred for 30 minutes. Then additional water (70 mL) was added and the reaction was stirred overnight under an atmosphere of nitrogen at room temperature. Water (50 mL) was added to the reaction, a distillation head was attached, the mixture was brought to reflux and distilled until the head temperature reached 100° C. The distillation head was removed and a reflux condenser was attached and the reaction was heated at reflux for 1 hour to give a clear orange solution with some dark gummy solid around the edges. The reaction was cooled slightly then the hot solution was decanted away from the gum into a 500 ml round bottomed flask. The solution was stirred and allowed to cool to room temperature then was made basic (pH 12) via dropwise addition of an aqueous 50% NaOH solution. Methylene chloride was added; the mixture was stirred well, and then was transferred to a separatory funnel. The organic layer was separated and the aqueous layer was repeatedly extracted with additional methylene chloride (until TLC analysis indicated that all product had been extracted from the aqueous layer). The organic extracts were combined, washed with saline, dried over sodium sulfate, filtered, and evaporated in vacuo to leave 2.53 g crude product as a light brown powder. LCMS: formic acid, [M+H++ Na+]=208; $^1$H NMR (400 MHz, DMSO) δ 7.31 (d, J=7.8 Hz, 1H), 7.24-7.15 (m, 2H), 4.79 (s, 1H), 4.20 (s, 1H), 4.01 (s, 1H), 2.92 (d, J=15.3 Hz, 1H), 2.73 (d, J=16.2 Hz, 1H), 2.15-1.43 (s, 2H). Chiral HPLC (Chiralpak AD 4.6×250 column eluted with 9550.1% hexane/EtOH/DEA @ 2.0 ml/min-45 min run) showed an ee of 80%.

Steps 3 and 4: Chiral Resolution of (1R,2S)-1-amino-5-chloroindan-2-ol (5)

To a flask containing a solution of rel-(1R,2S)-1-amino-5-chloroindan-2-ol (3) (2.53 g, 13.8 mmol) in methanol (100 mL) at reflux was added D-(–)-mandelic acid (2.09 g, 13.8 mmol) with stirring. After refluxing for ~15 min the heating mantle was removed and the solution was allowed to cool to room temperature with stirring. Solids began precipitating ~15 minutes after the heat source had been removed. The resulting mixture was stirred overnight at rt. The mixture was then filtered, washed with methanol (10 mL) then diethyl ether (15 mL) and dried in vacuo to provide 2.50 g of the intermediate salt. The filtrate was concentrated to ~⅓ volume and refrigerated overnight, during which time more product precipitated. Again, the mixture was filtered and washed with methanol (7.5 mL) then diethyl ether (10 mL) and dried in vacuo to provide an additional 0.60 g of the intermediate salt. A total of 3.1 g was collected.

The intermediate salt was stirred in a mixture of ethyl acetate (50 ml) and aqueous NaOH (0.2M, 60 ml) until dissolution was complete. The mixture was transferred to a separatory funnel and the organic layer was separated. The aqueous layer was further extracted with ethyl acetate (3×50 ml). The combined organic layers were washed with saline until the washings were neutral, then were dried over sodium sulfate, filtered, and evaporated to leave a light tan solid. Further drying under hi-vacuum yielded 1.42 g (56% yield) of the title compound as a light tan powder. Analytical data for title compound: $^1$H NMR (400 MHz, DMSO) δ 7.31 (d, J=7.9 Hz, 1H), 7.24-7.15 (m, 2H), 4.83 (s, 1H), 4.20 (t, J=3.9 Hz, 1H), 4.00 (d, J=4.5 Hz, 1H), 2.92 (dd, J=16.2, 4.9 Hz, 1H), 2.73 (d, J=15.2 Hz, 1H), 1.85 (s, 2H). Chiral HPLC (Chiralpak AD 4.6×250 column eluted with 9550.1% hexane/EtOH/DEA @ 2.0 ml/min-45 min run) showed an ee of >99%.

Step 5: 2-[(1R,2S)-5-chloro-2-hydroxy-2,3-dihydro-1H-inden-1-yl]-1H-isoindole-1,3(2H)-dione (6)

In a 1 L round bottom flask, N,N-diisopropylethylamine (15.2 mL, 0.0871 mol) was added to a suspension of (1S,2R)-1-amino-5-chloroindan-2-ol (16.0 g, 0.0871 mol) and phthalic anhydride (14.2 g, 0.0958 mol) in toluene (473 mL, 4.44 mol), and the reaction mixture was heated at reflux for 18 hours. The reaction was cooled to room temperature, at which point a large amount of solid precipitated. The solid, which was the desired product, was filtered, rinsed with EtOAc and collected. The filtrate was cooled to 0° C., filtered and the solid was rinsed with EtOAc and combined with the first batch. The filtrate was transferred to a separatory funnel and diluted with $H_2O$ (200 mL). The layers were separated, and the aqueous layer was extracted EtOAc (3×200 mL). The combined organic layers were washed 1× brine (100 mL), dried over $MgSO_4$, filtered, and concentrated in vacuo. The resulting off-white solid was suspended in EtOAc, the large chunks were broken up with sonication, and the suspension was cooled to 0° C. The solid was filtered and combined with the previous 2 batches. The filtrate was concentrated in vacuo, and the resultant white solid was suspended one final time in $Et_2O$ (100 mL), filtered and combined with the previous 3 batches. The total yield of all four batches of solid was 25.3 g (92%). LCMS: (FA) ES+ molecular ion 314, major ionization 167; $^1$H NMR (400 MHz, DMSO) δ 7.83 (s, 4H), 7.33 (s, 1H), 7.27 (d, J=8.2, 1H), 7.19 (dd, J=2.0, 8.1, 1H), 5.52 (d, J=7.4, 1H), 5.34 (d, J=5.2, 1H), 4.64 (dt, J=6.9, 12.7, 1H), 3.21 (dd, J=7.4, 16.1, 1H), 3.02 (dd, J=6.1, 16.1, 1H).

Step 6: 2-[(1R,2S)-5-chloro-2-methoxy-2,3-dihydro-1H-inden-1-yl]-1H-isoindole-1,3(2H)-dione (7)

To a solution of 2-[(1R,2S)-5-chloro-2-hydroxy-2,3-dihydro-1H-inden-1-yl]-1H-isoindole-1,3(2H)-dione (25.8 g, 0.0822 mol) in tetrahydrofuran (186 mL, 2.29 mol) was added methyl iodide (20.5 mL, 0.329 mol) and the solution was stirred at 0° C. To this solution was added 1.00 M of potassium tert-butoxide in tetrahydrofuran (90.4 mL, 0.0904 mol) dropwise via an addition funnel over 1 hour. The reaction was quenched via addition of 0.1 N HCl (250 mL) and transferred to a separatory funnel containing EtOAc (600 mL). The layers were separated, and the organic layer was washed with 1N NaOH (2×100 mL each) and with brine (100 mL). The organic layer was dried over $Na_2SO_4$, filtered, and concentrated to afford 2-[(1R,2S)-5-chloro-2-methoxy-2,3-dihydro-1H-inden-1-yl]-1H-isoindole-1,3 (2H)-dione (25.8 g, 96%) which was used without further purification in the next step.

Step 7: (1R,2S)-5-chloro-2-methoxyindan-1-amine (8)

To a suspension of 2-[(1R,2S)-5-chloro-2-methoxy-2,3-dihydro-1H-inden-1-yl]-1H-isoindole-1,3(2H)-dione (7) (25.8 g, 0.0787 mol) in ethanol (260 mL, 4.4 mol) was added hydrazine (4.94 mL, 0.157 mol), and the flask was affixed with a reflux condenser and heated to a bath temperature of 90° C. A precipitate began to form after several minutes of stirring and after 1 hour of heating the mixture had become a thick slurry/solid. The reaction was cooled to room temperature and the solid reaction byproducts were filtered and washed with CH$_2$Cl$_2$ (~300 mL). The volatiles were removed from the filtrate in vacuo, and the residue was suspended in CH$_2$Cl$_2$ (250 mL), at which point the solid byproducts were again removed by filtration. The volatiles were removed in vacuo, and the residue was again suspended in CH$_2$Cl$_2$ (~50 mL). The solid byproducts were removed a final time by filtration to afford (1R,2S)-5-chloro-2-methoxyindan-1-amine (15.5 g, 99%) as a red/orange waxy solid. LCMS: (FA) ES+ molecular ion 198, major ionization 181; $^1$H NMR (400 MHz, DMSO) δ 7.30 (d, J=7.9, 1H), 7.25-7.16 (m, 2H), 4.14 (d, J=4.9, 1 H), 3.89 (td, J=2.8, 4.9, 1 H), 3.29 (s, 3H), 2.89 (ddd, J=3.8, 16.4, 21.3, 2H), 2.04 (s, 2H). Chiral HPLC (Chiralpak AD 4.6×250 column eluted with 9550.1% hexane/EtOH/DEA @ 1.0 ml/min-30 min run) showed an ee of >99%.

Example 2. Synthesis of {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216)

Step 1: rel-(1R,5R)-5-({[tert-butyl(dimethyl)silyl]oxy}methyl)cyclopent-2-en-1-ol (10)

To a solution of rel-(1R,5R)-5-(hydroxymethyl)cyclopent-2-en-1-ol (47.20 g, 0.4135 mol), N,N-dimethylaminopyridine (2.52 g, 0.0207 mol) and 1H-imidazole (30.97 g, 0.4549 mol) in methylene chloride (800 mL, 10 mol) at 0° C. under an atmosphere of nitrogen was added tert-butyldimethylsilyl chloride (28.0 g, 0.186 mol). The reaction was stirred for at 0° C. for 2.5 h, at which time tart-butyldimethylsilyl chloride (28.0 g, 0.186 mol) was added. The reaction was stirred for 2 additional hours. The reaction was quenched by addition of saturated aqueous NaCl solution (200 mL) and water (200 mL). The layers were separated and the organic layer was washed with water (3×200 mL) and brine (1×200 mL), dried over Na$_2$SO$_4$, filtered and concentrated in vacuo. The material was used without further purification in the next step.

Step 2: (1S,5S)-5-({[tert-butyl(dimethyl)silyl]oxy}methyl)cyclopent-2-en-1-ol (11)

To a suspension of rel-(1R,5R)-5-({[tert-butyl(dimethyl)silyl]oxy}methyl)-cyclopent-2-en-1-ol (crude (10) from previous step) and *Candida Antarctica* on acrylic resin (24.9 g; 10,800 units/g) in methyl tert-butyl ether (1500 mL, 10 mol) was added acetic acid ethenyl ester (190 mL, 2.05 mol) and the reaction was stirred overnight. Solids were removed by filtration and the volatiles were removed in vacuo to provide a clear-colorless oil (143 grams) which was purified by column chromatography (1 kg silica gel column, eluent 0-30% Et$_2$O:hexanes) to afford the desired enantiomer (1S,5S)-5-({[tert-butyl(dimethyl)silyl]oxy}methyl)cyclopent-2-en-1-ol (37.5 grams, 79.5%). Chiral HPLC; Chiral Technologies Chiralpak AS RH (4.6×150 mm) 5 micron column, eluent—55% (0.1% formic acid in 99:1 H$_2$O/CH$_3$CN), 45% (0.1% formic acid in 95:5 CH$_3$CN/H$_2$O) indicated an ee of >99%. $^1$H NMR (400 MHz, CDCl$_3$) δ 5.96-5.91 (m, 1H), 5.86-5.80 (m, 1H), 4.87 (dd, J=2.3, 4.9, 1H), 3.87 (dd, J=4.7, 10.1, 1H), 3.79 (dd, J=7.7, 10.1, 1H), 2.50-2.40 (m, 1H), 2.35 (ddt, J=2.0, 8.4, 16.8, 1H), 2.23-2.14 (m, 1H), 0.90 (s, 9H), 0.08 (s, 3H), 0.07 (s, 3H). The undesired enantiomer was isolated as the corresponding acetate in 81.6% yield.

Step 3: tert-butyl[((1S,2S)-2-{[tert-butyl(dimethyl)silyl]oxy}cyclopent-3-en-1-yl)methoxy]dimethylsilane (12)

In an oven-dried 2 L two-neck flask, cooled under nitrogen, to a solution of (1S,5S)-5-({[tert-butyl(dimethyl)silyl]oxy}methyl)cyclopent-2-en-1-ol (11) (98.07 g, 0.3864 mol) in methylene chloride (500 mL, 8 mol) was added 1H-imidazole (31.57 g, 0.4637 mol). To the resulting yellow solution was added a solution of tert-butyldimethylsilyl chloride (58.2 g, 0.386 mol) in methylene chloride (300 mL, 5 mol) via addition funnel over ~30 min. The mixture was stirred mechanically for 18 hours. The reaction was quenched via addition of water (500 mL) and the layers were separated. The organic layer was washed with water (2×500 mL), dried over MgSO$_4$, filtered, and concentrated in vacuo to afford tert-butyl[((1S,2S)-2-{[tert-butyl(dimethyl)silyl]oxy}cyclopent-3-en-1-yl)methoxy]dimethylsilane (143.3 g) as a crude residue that was used without further purification.

Step 4: (1R,3S,4S)-3-{[tert-butyl(dimethyl)silyl]oxy}-4-({[tert-butyl(di-methyl)silyl]oxy}methyl)cyclopentanol (13)

In a 2 L round bottomed flask, tert-butyl[((1S,2S)-2-{[tert-butyl(dimethyl)silyl]oxy}cyclopent-3-en-1-yl)methoxy]dimethylsilane (12) (12.08 g of the crude residue) was azeotroped with toluene three times, dried under vacuum for 30 minutes, and dissolved in anhydrous tetrahydrofuran (402.7 mL) under an atmosphere of argon. To the solution was added catecholborane in tetrahydrofuran (1.00 M, 88.1 mL, 0.0881 mol) dropwise. Argon was then bubbled through for 20 minutes to deoxygenate the reaction solution. Tris(triphenylphosphine)rhodium(I) chloride (3.26 g, 0.00352 mol) was then added, and the reaction was stirred for 18 hours at room temperature under argon. To the reaction was added 1.00 M of sodium hydroxide in water (528.8 mL, 0.5288 mol), followed by careful addition of hydrogen peroxide solution (35 wt % in water, 30.79 mL, 0.3525 mol), and the mixture was stirred for 4 hours at room temperature. Reaction was quenched via addition of saturated Na$_2$S$_2$O$_3$ (500 mL), the layers were separated, and the aqueous layer was extracted with EtOAc (2×300 mL). The combined organic portions were washed with brine, dried over Na$_2$SO$_4$, filtered, and concentrated in vacuo. The brown oil was purified by column chromatography (eluent 0% to 20% ether in hexanes) to afford (1R,3S,4S)-3-{[tert-butyl(dimethyl)silyl]oxy}-4-({[tert-butyl(di-methyl)silyl]oxy}methyl)cyclopentanol (7.78 g, 2 steps yield=66%). $^1$H NMR (400 MHz, CDCl$_3$) δ 4.50 (d, J=4.3, 1 H), 4.34 (td, J=2.7, 4.8, 1 H), 3.71 (dd, J=7.0, 10.0, 1 H), 3.53 (dd, J=7.0, 10.0, 1H), 2.32® 2.20 (m, 1H), 2.04 (ddd, J=2.6, 6.7, 13.9, 1H), 1.85 (ddd, J=7.1, 10.3, 13.5, 1H), 1.73 (dt, J=4.8, 13.9, 1H), 1.63 (ddd, J=2.1, 7.9, 13.5, 1H), 1.35 (s, 1H), 0.88 (s, 9H), 0.86 (s, 9H), 0.04 (s, 3H), 0.03 (s, 9H).

Step 5: 4-{[(1R,3S,4S)-3-{[tert-butyl(dimethyl)silyl]oxy}-4-({[tert-butyl(dimethyl)silyl]oxy}methyl)cyclopentyl]oxy}-6-chloropyrimidine (14)

A flame-dried 50 mL round bottom flask with was charged with sodium hydride (0.322 g, 0.008 mol) and tetrahydrofuran (20 mL, 0.3 mol) and the resulting suspension was cooled to 0° C. under an atmosphere of nitrogen. To the suspension was added dropwise a solution of (1R,3S,4S)-3-{[tert-butyl(dimethyl)silyl]oxy}-4-({[tert-butyl(dimethyl)silyl]oxy}methyl)cyclopentanol (13) (1.45 g, 0.004 mol) in 0.5 mL THF at 0° C. The mixture was stirred at 0° C. for 10 minutes, at which point 4,6-dichloropyrimidine (0.659 g, 0.004 mol) was added, and the mixture was allowed to warm to room temperature and stirred for 18 hours. The reaction was quenched with via addition of saturated aqueous NH$_4$Cl solution (25 mL) and transferred to a separatory funnel. The layers were separated, and the aqueous layer was extracted with tert-BuOMe (3×25 mL). The combined organic layers were washed with brine, dried over anhydrous MgSO$_4$, filtered, and concentrated in vacuo. The resulting oil was purified by silica gel chromatography (eluent—0-10% EtOAc in hexanes) to afford 4-{[(1R,3S,4S)-3-{[tert-butyl(dimethyl)silyl]oxy}-4-({[tert-butyl(dimethyl)silyl]oxy}methyl)cyclopentyl]oxy}-6-chloropyrimidine (1.75 g, 92% yield). LCMS: (FA) ES+ 473; $^1$H NMR (300 MHz, CDCl$_3$) δ 8.55 (d, J=0.7, 1 H), 6.69 (d, J=0.8, 1 H), 5.61-5.49 (m, 1H), 4.36 (dd, J=4.6, 6.8, 1H), 3.73 (dd, J=7.0, 10.0, 1H), 3.57 (dd, J=6.7, 9.9, 1H), 2.36-2.13 (m, 2H), 2.10-1.73 (m, 3H), 0.89 (s, 9H), 0.88 (s, 9H), 0.08-0.00 (m, 12H).

Step 6: {(1S,2S,4R)-2-{[tert-butyl(dimethyl)silyl]oxy}-4-[(6-chloropyrimidin-4-yl)oxy]cyclopentyl}methanol (15)

In a 2 L round-bottomed flask, 4-{[(1R,3S,4S)-3-{[tert-butyl(dimethyl)silyl]-oxy}-4-({[tert-butyl(dimethyl)silyl]oxy}methyl)cyclopentyl]oxy}-6-chloropyrimidine (14) (20.5 g, 0.0433 mol was dissolved in ethanol (647.2 mL, 11.08 mol), and cooled to an internal temp of −45° C. To this was added a precooled (−20° C.) solution of 2% conc. HCl in EtOH (326 mL, 0.0516 mol, prepared by diluting 6.5 mL conc. HCl in 319.5 mL ethanol). The reaction mixture was warmed to −25° C. (to prevent pressure buildup upon capping the flask), and then capped and placed in a freezer at −35° C. The reaction was left to stand at −35° C. for 18 hours. The reaction was quenched with sodium carbonate (13.78 g, 0.1300 mol) (~3 equiv relative to HCl) as a solution in water (40 mL, 2 mol). The volatiles were removed in vacuo, and the reaction mixture was diluted with CH$_2$Cl$_2$ (750 mL). The solids were filtered and set aside, and the volatiles were removed from the filtrate in vacuo. The resulting aqueous mixture with was diluted with EtOAc (500 mL) and water (200 mL) and transferred to a separatory funnel. The layers were separated, and the aqueous layer was extracted 2×250 mL with EtOAc. The combined organic layers were dried over Na$_2$SO$_4$, filtered, and concentrated in vacuo. The crude residue was purified by column chromatography (applied to column with ~50 mL CH$_2$Cl$_2$, 400 g column, eluent 0-40% EtOAc:hexanes over 40 min to afford {(1S,2S,4R)-2-{[tert-butyl(dimethyl)silyl]oxy}-4-[(6-chloropyrimidin-4-yl)oxy]cyclopentyl}methanol (11.2 g, 72%). LCMS: (FA) ES+ 359; $^1$H NMR (400 MHz, CDCl$_3$) δ 8.56 (app d, J=0.6, 1H), 6.70 (app d, J=0.8, 1H), 5.62-5.54 (m, 1H), 4.56 (dd, J=5.6, 10.9, 1H), 3.86-3.78 (m, 1H), 3.70 (ddd, J=6.0, 7.6, 11.3, 1H), 2.48 (dd, J=4.6, 7.6, 1H), 2.42-2.31 (m, 1H), 2.23 (ddd, J=6.3, 9.8, 14.2, 1H), 2.15-2.09 (m, 2H), 1.89 (ddd, J=1.9, 8.0, 14.3, 1H), 0.91 (s, 9H), 0.12 (s, 3H), 0.11 (s, 3H).

Step 7: {(1S,2S,4R)-2-{[tert-butyl(dimethyl)silyl]oxy}-4-[(6-{[(1R,2S)-5-chloro-2-methoxy-2,3-dihydro-1H-inden-1-yl]amino}pyrimidin-4-yl)oxy]cyclopentyl}methanol (16)

To a solution of {(1S,2S,4R)-2-{[tert-butyl(dimethyl)silyl]oxy}-4-[(6-chloropyrimidin-4-yl)oxy]cyclopentyl}methanol (15) (11.2 g, 0.0312 mol) and N,5-dichloro-2-methoxy-2,3-dihydro-1H-inden-1-amine (9.00 g, 0.0384 mol) in 1-butanol (99.2 mL, 1.09 mol), in a 350 mL sealable reaction vessel, was added triethylamine (21.7 mL, 0.156 mol). The vessel was sealed and then heated with stirring to 148° C. in an oil bath for 72 hours. The vessel was cooled to room temperature and the volatiles were removed in vacuo and Et$_2$O (200 mL) was added to the resulting residue. The solids were homogenized by sonication, filtered, and rinsed with Et$_2$O (50 mL). To the filtrate was added Celite® (100 mL) and the volatiles were removed in vacuo. The product adsorbed onto Celite® was added to a dry load cartridge and purified via column chromatography (400 g column, eluent 0-80% EtOAc:hexanes over 80 min) to afford {(1S,2S,4R)-2-{[tert-butyl(dimethyl)silyl]oxy}-4-[(6-{[(1R,2S)-5-chloro-2-methoxy-2,3-dihydro-1H-inden-1-yl]amino}pyrimidin-4-yl)oxy]cyclopentyl}methanol (11.5 g, 71%). LCMS: (FA) ES+ 520; $^1$H NMR (400 MHz, CDCl$_3$) δ 8.31 (s, 1H), 7.24-7.13 (m, 3H), 5.75 (s, 1H), 5.56 (s, 1H), 5.45 (dt, J=2.9, 5.8, 2H), 4.57 (dd, J=5.9, 11.2, 1H), 4.19 (td, J=1.3, 4.7, 1H), 3.84-3.77 (m, 1H), 3.75-3.65 (m, 1H), 3.37 (s, 31-1), 3.10 (d, J=16.6, 1H), 2.97 (dd, J=4.5, 16.7, 1H), 2.58 (dd, J=4.8, 7.4, 1H), 2.43-2.32 (m, 1H), 2.23-2.06 (m, 3H), 1.90 (dd, J=8.0, 14.2, 1H), 0.91 (s, 9H), 0.11 (s, 3H), 0.10 (s, 3H).

Step 8: {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216)

To a solution of {(1S,2S,4R)-2-{[tert-butyl(dimethyl)silyl]oxy}-4-[(6-{[(1R,2S)-5-chloro-2-methoxy-2,3-dihydro-1H-inden-1-yl]amino}pyrimidin-4-yl)oxy]cyclopentyl}methanol (16) (11.5 g, 0.0221 mol) in N,N-dimethylacetamide (160 mL, 1.7 mol) was added chlorosulfonamide (6.64 g, 0.0575 mol), and the reaction stirred at room temperature for 1 hour. The reaction mixture was then cooled to 0° C., at which point 12 M hydrochloric acid (90 mL, 1.1 mol) was added dropwise via an addition funnel over 25 min, keeping the internal reaction temp below 50° C. Once the addition was complete, the cooling bath was removed and the reaction was allowed to warm to room temperature with stirring for 2 hours. The reaction was next quenched carefully via slow addition of a suspension of sodium carbonate (70.30 g, 0.6633 mol) in water (200.0 mL, 11.10 mol). The resulting suspension was filtered and the solids were rinsed with EtOAc (3 rinses, total—800 mL). The solids were set aside, and the filtrate was transferred to a separatory funnel and the layers were separated. The aqueous layer was extracted 3×EtOAc (total EtOAc—2000 mL), and, the combined organic layers were dried over Na$_2$SO$_4$, filtered, and concentrated in vacuo. The crude residue was purified via column chromatography (applied with CH$_2$Cl$_2$, 400 g column, eluent 0-10% MeOH:CH$_2$Cl$_2$ over 80 min then 10% MeOH:CH$_2$Cl$_2$ for 20 min) to afford {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (10.3 g, 96%). LCMS: (FA) ES+ 485; $^1$H NMR (400 MHz, MeOD) δ 8.16 (s, 1H), 7.25 (s, 1H), 7.22-7.13 (m, 2H), 5.98 (s, 1H), 5.52 (d, J=32.8, 1H), 5.34 (s, 1H), 4.43-4.35 (m, 1H), 4.32 (dd, J=7.5, 9.8, 1H), 4.22 (td, J=2.5, 5.0, 1H), 4.16 (dd, J=7.3, 9.8, 1H), 3.34 (s, 4H), 3.10 (dd, J=2.1, 16.6, 1H), 3.02 (dd, J=4.8, 16.6, 1H), 2.58-2.46 (m, 1H), 2.28 (ddd, J=2.2, 6.9, 14.8, 1H), 2.12-1.90 (m, 4H).

Step 9: {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate HCl salt (I-216 HCl Form I)

{(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216) (24.1 g, 0.0497 mol) was placed in a 500-ml rbf equipped with a stirbar. Acetonitrile (500 mL) was added with stirring. The mixture was sonicated for one minute and then was stirred at room temperature under an atmosphere of nitrogen for 1 hour to ensure that the solid was fully dispersed. Aqueous hydrochloric acid (6.0M, 9.15 mL, 0.0549 mol) was added in a slow stream—the solution became looser but total solution did not occur. The mixture was seeded with a few crystals of previously prepared I-216 HCl salt (prepared, as described in Example 3 below) and the mixture was sonicated for 1 minute then was stirred at room temperature under an atmosphere of nitrogen for 2 hours; the mixture became quite thick during this time as white solid precipitated from solution. The stirred mixture was diluted with diethyl ether (500 mL) and then stored in a refrigerator overnight. The precipitate was collected on a fritted glass funnel, washed with ether, then dried in vacuo overnight at 40° C. to leave the title compound as a fluffy white crystalline powder, 24.37 g (94% yield). $^1$H NMR (400 MHz, DMSO) δ 8.44 (s, 1H), 8.38 (s, 2H), 7.43 (s, 2H), 7.36 (s, 1H), 7.23 (dd, J=20.1, 8.1 Hz, 3H), 6.22 (s, 1H), 5.68 (s, 1H), 5.26 (s, 1H), 4.31-4.12 (m, 4H), 4.09-3.92 (m, 1H), 3.05 (s, 3H), 2.36 (dt, J=18.8, 7.6 Hz, 1H), 2.21 (dd, J=14.0, 6.5 Hz, 1H), 2.05-1.93 (m, 2H), 1.89 (dd, J=13.3, 8.3 Hz, 1H). LCMS: formic acid, [M+H+]=485.3. Chiral HPLC (Chiralcel OJ 4.6×250 column eluted with 60/40/0.1% hexane/EtOH/DEA @ 0.75 ml/min-60 min run) indicated product was 99.7% ee. HPLC analysis indicated that the product was 99.2% pure. XRPD data for I-216 HCl Form I produced in this Example 2 is shown in FIG. 7. Peaks identified in FIG. 7 include those listed in Table 5.

TABLE 5

| Angle 2-Theta ° | Intensity % |
|---|---|
| 4.759 | 56.2 |
| 7.807 | 81.1 |
| 9.16 | 27.8 |
| 10.089 | 42.6 |
| 13.512 | 29.6 |
| 14.748 | 78.7 |
| 14.812 | 71.9 |
| 15.486 | 89.9 |
| 16.166 | 68.6 |
| 17.151 | 26.3 |
| 17.484 | 38.5 |
| 18.13 | 29 |
| 18.255 | 23.3 |
| 18.519 | 42.6 |
| 19.439 | 37.9 |
| 19.729 | 53.8 |
| 20.296 | 37.9 |
| 21.581 | 77.5 |
| 22.065 | 100 |
| 22.391 | 48.5 |
| 22.662 | 60.9 |
| 22.993 | 66.3 |
| 23.323 | 37.5 |
| 23.796 | 45.6 |
| 24.289 | 81.7 |
| 25.086 | 63.3 |

TABLE 5-continued

| Angle 2-Theta ° | Intensity % |
|---|---|
| 25.927 | 43.8 |
| 26.678 | 52.7 |
| 26.961 | 47.1 |
| 27.069 | 50.1 |
| 28.185 | 26 |
| 28.63 | 26.6 |
| 29.277 | 29.6 |

DSC data for I-216 HCl Form I produced in this Example 2 is shown in FIG. 8, and TGA data for I-216 HCl Form I produced in this Example 2 is shown in FIG. 9.

Example 3. Synthesis of {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate hydrochloride salt (I-216 HCl)

{(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate I-216 (4.44 g, 0.00916 mol) was placed in a 250-ml round bottomed flask equipped with a stir bar. Acetonitrile (82.5 mL) was added with stirring. The mixture was stirred and sonicated for several minutes (the solids did not fully dissolve). The flask was immersed in an ice bath and then, with stirring, aqueous hydrochloric acid (6.0M, 1.69 mL, 0.0101 mol) was added in a slow stream during which time the solids partially dissolved. The ice bath was removed and the reaction mixture was stirred at room temperature under an atmosphere of nitrogen for 2 hours during which time a dense white precipitate formed. Diethyl ether (82.5 mL) was added with stirring and the resulting mixture was stored in a refrigerator overnight. The precipitated product was collected on a fritted funnel, washed with cold ether, then dried for 24 hours at 42° C. under high vacuum to afford the title compound as a fluffy white powder, 3.84 g (80% yield). LCMS: formic acid, [M+H+]=485.2. 1H NMR (400 MHz, MeOD) δ 8.42 (s, 1H), 7.30 (s, 1H), 7.27-7.18 (m, 2H), 6.26 (s, 1H), 5.78 (s, 1H), 5.30 (s, 1H), 4.46-4.38 (td, J=5.2, 2.0 Hz, 1H), 4.39-4.25 (m, 2H), 4.23-4.13 (dd, J=9.9, 7.4 Hz, 1H), 3.37 (s, 3H), 3.18-3.04 (m, 2H), 2.62-2.47 (m, 1H), 2.42-2.31 (ddd, J=15.0, 6.9, 2.0 Hz, 1H), 2.24-2.14 (dt, J=15.0, 4.6 Hz, 1H), 2.14-2.02 (dd, J=10.3, 5.9 Hz, 2H).

Example 4. Synthesis of (1R,2S)-5-chloro-2-methoxy-2,3-dihydro-1H-inden-1-amine hydrochloride (20)

Step 1: 5-chloro-2-methoxy-2,3-dihydro-1H-inden-1-one (18)

A 22 L multi-neck reactor equipped with a temperature probe, a nitrogen inlet, a cooling bath and an overhead mechanical stirrer was charged with methanol (2400 mL) and cooled to −20° C. Sulfuric acid (384 mL, 7.22 mol) was charged via an addition funnel over 1 hour. The temperature was maintained at about −25° C. and peaked at −18° C. for ~5 minutes. Trimethyl orthoformate (906 mL, 8.3 mol) was added over 10 minutes followed by 5-chloro-2,3-dihydro-1H-inden-1-one (17) (600.00 g, 3.61 mol) as a solid. The internal temperature slightly increased by 2° C. Koser's reagent (1553 g, 3.97 mol) was dissolved in methanol (2400 mL) over 20 minutes which was added to the reaction vessel over 1 hour and 15 minutes. The addition was exothermic and the internal temperature was maintained at about −20° C. Upon completion of addition, the dark red solution was stirred at −20° C. for 1 hour, at which point HPLC analysis indicated complete conversion to the desired product. Water (7200 mL) was added in small portions. After the addition of a small amount of water (~50 mL), the product suddenly precipitated. The agitation became slow and difficult. The mixture was stirred at 0~10° C. for 1 hour and was filtered through a 3000 mL coarse fritted funnel. The filtration was complete in 2 hours and the cake was rinsed with water (7200 mL) until the pH of the filtrate reached about 5. The wet cake was added back to the reactor and heptane (3000 mL) was added. The mixture was stirred at −20° C. for 1 h and filtered. The cake was rinsed with heptanes (1200 mL) and conditioned for 30 minutes. The wet cake was dried under high vacuum for 3 days to completely remove heptane and reduce the water content to <2%. The material had purities of 99% (AUC by HPLC) and 93 wt % by wt % assay (622.88 g, 88%). $^1$H NMR (300 MHz, CDCl3, δ): 7.69 (m, 1H), 7.43 (s, 1H), 7.38 (m, 1H), 4.18 (m, 1H), 3.63 (s, 3H), 3.47 (m, 1H) and 2.99 (m, 1H).

Step 2: (R,E)-N-((S)-5-chloro-2-methoxy-2,3-dihydro-1H-inden-1-ylidene)-2-methylpropane-2-sulfinamide (19)

A 22 L multi-neck reactor equipped with a condenser, a nitrogen inlet, a heating mantle and an overhead mechanical stirrer was charged with 5-chloro-2-methoxy-2,3-dihydro-1H-inden-1-one (18) (622.88 g, 3.17 mol) and (R)-tart-butylsulfinamide (460.7 g, 3.8 mol). Tetrahydrofuran (3100 mL) was added to the mixture and the temperature dropped to 9° C. Ti(OEt)$_4$ (985 mL, 4.76 mol) was added over 10 minutes. The mixture was heated to 68° C. and all solids dissolved at about 35° C. After 5 hours, the reaction achieved a 50% yield as determined by HPLC wt % assay. The reaction was stirred at 68° C. for an additional 5 hours until the undesired diastereomer decomposed to less than 5% (AUC). The reaction was cooled to ambient temperature over 2 hours and stirred for 16 hours. HPLC analysis indicated no obvious change in reaction profile during this period. This crude reaction mixture was taken in to the next step without further purification.

Step 3 and 4: (1R,2S)-5-chloro-2-methoxy-2,3-dihydro-1H-inden-1-amine hydrochloride (20)

A 22 L multi-neck reactor equipped with a nitrogen inlet, a cooling bath and an overhead mechanical stirrer was charged with crude (R,E)-N-((S)-5-chloro-2-methoxy-2,3-dihydro-1H-inden-1-ylidene)-2-methylpropane-2-sulfinamide (21) [approximately 475 g, approximately 1.58 mol] in tetrahydrofuran (4000 mL). Methanol (9300 mL) was added in small portions. No obvious temperature change was observed. The mixture was cooled to −24° C. using an acetone/dry ice bath. A 2 L, three-neck round bottom flask was charged with triglyme (528 mL) and cooled to 9° C. NaBH$_4$ (60.2 g, 1.58 mol) was added in small portions. The temperature slightly increased by 1° C. The mixture was warmed to ambient temperature and stirred for 2 hours until all solids dissolved to afford a slightly cloudy solution. The NaBH$_4$ solution was charged to the 22 L reactor over 50 minutes at −24° C. The exotherm was controlled by the addition rate. No obvious off-gassing was observed. Upon completion of addition, the mixture was stirred at −24° C. for an additional 2 hours, at which point HPLC analysis indicated a complete reaction and a 92% dr. The mixture was warmed up to ambient temperature over 3 hours and stirred for 16 hours. The reaction was cooled again to ~7° C. and water (950 mL) was added in portions resulting in a 5° C. increase of the internal temperature. Celite (475 g) was added and the Mixture was stirred for 1 hour. The mixture was then filtered through a large bench-top filter (i.d.: 19 in) and the filter cake was rinsed with methanol (4000 mL). HPLC analysis of the last portion of filtrate indicated no significant amount of product. The combined filtrates, were concentrated under reduced pressure to a volume of ~6 L. Isopropyl acetate (950 mL) was added and the layers were allowed to separate. The aqueous layer was extracted with isopropyl acetate (900 mL) and the combined organic layer was washed with saturated brine (2000 mL). The solution was then dried over sodium sulfate and concentrated to about 2 L. The mixture was then azeotropically distilled with tetrahydrofuran (3000 mL×2). Karl-Fisher analysis indicated a water content of ~0.2%.

A 22 L multi-neck reactor equipped with a nitrogen inlet, a cooling bath and an overhead mechanical stirrer was charged with crude sulfonyl intermediate (approximately 475 g, approximately 1.58 mol) and 2-methyl-tetrahydrofuran (9500 mL). The solution was cooled to −20° C. and 4M hydrochloric acid in dioxane (800 mL, 3.16 mol) was added over 40 minutes. An exotherm was not obvious. Product precipitated out toward the end of the addition. The mixture was stirred at −20° C. for an additional 1 hour, at which point HPLC analysis indicated complete conversion. The mixture was filtered through a large Büchner funnel (i.d.: 11 in). The filtration took over 2 hours. The filter cake was rinsed with acetone (1000 mL) and conditioned for 1 hour. The solid was then transferred back to the reactor and acetone (3500 mL) was added. The mixture was stirred at ambient temperature for 16 hours and then filtered. The filter cake was rinsed with acetone (500 mL) and then dried under vacuum for 16 hours. Approximately 293 g of product was afforded as an off-white solid. HPLC analysis indicated 96% purity and 96% vs. A 22 L, multi-neck reactor equipped with a condenser, a nitrogen inlet, a heating mantle and an overhead mechanical stirrer was charged with (1R,2S)-5-chloro-2-methoxy-2,3-dihydro-1H-inden-1-amine hydrochloride (20) (290 g, 1.24 mol) and ethanol (5200 mL). The mixture was stirred for 1 hour and a slightly cloudy solution was afforded. The mixture was filtered through a fine fritted funnel and the clear filtrate was charged back to the reactor. The solution was heated to 55° C. and stirred for 30 minutes. 2-methoxy-2-methylpropane (5200 mL) was added over 1.5 hours and the temperature was maintained at 55° C. during the addition. Solid precipitated toward the end of the addition. The resulting white suspension was stirred at 55° C. for 1 hour and slowly cooled to ambient temperature over 2 hours. The mixture was stirred at ambient temperature for 2 days and then filtered through a large Büchner funnel (Id.: 11 in). The filter cake was rinsed with MTBE (1000 mL) and dried under vacuum for 16 hours. The product was afforded as a white solid (184.4 g, 50%, >99% AUC, >99% ee). $^1$H NMR (300 MHz, CD3OD, δ): 7.50 (m, 1H), 7.37 (m, 2H), 4.78 (m, 1H), 4.40 (m, 1H), 3.51 (s, 3H) and 3.19 (m, 1H).

Example 5. Synthesis of (((1S,2S,4R)-4-(6-((1R,2S)-5-chloro-2-methoxy-2,3-dihydro-1H-inden-1-ylamino)pyrimidin-4-yloxy)-2-hydroxycyclopentyl) methyl sulfamate hydrochloride Form I (I-216 HCl Form I)

Step 1: ((1R,4S)-4-(benzyloxy)-3-(benzyloxymethyl)cyclo nyloxy)trimethylsilane (22)

To a solution of dipropylamine (212 mL, 1.55 mol) in 2-methoxy-2-methylpropane (2000 mL) at −15° C. under a blanket of nitrogen, 2.50 M of n-butyllithium in hexane (567 mL, 1.42 mol) was added slowly over 10 minutes, maintaining a temperature of less than −10° C. The resulting white suspension was stirred for 30 minutes at −15° C. To this suspension was added (1S,2R,3S,5R)-3-(benzyloxy)-2-(benzyloxymethyl)-6-oxabicyclo[3.1.0]hexane (21) (400.00 g, 1.29 mol) slowly as a solution in methyl tert-butyl ether (1200 mL) over 30 minutes, maintaining an internal temperature of less than −10° C. The reaction mixture was stirred for 30 minutes at −15° C. TLC analysis indicated no remaining starting material (20% ethyl acetate/heptane). Chlorotrimethylsilane (204 mL, 1.61 mol) was added while maintaining a temperature of less than −10° C. The mixture was allowed to warm to 0° C. and stirred for 30 minutes. TLC analysis indicated that no alcohol intermediate (20% ethyl acetate heptane). The reaction mixture was quenched with the slow addition of water (4 L) while maintaining an internal temperature of less than 8° C. The aqueous layer was separated and the organic layer was extracted 3 times with water (3×4 L) and once with saturated sodium chloride in water (4 L). The organic layer was concentrated under reduced pressure to give an orange oil (480 g, 97.4%) which was used without further purification. $^1$H NMR (300 MHz, CD3OD, δ): 7.18 (m, 10H), 5.65 (s, 1H), 4.55 (t, 1H), 4.30 (m, 5H), 4.02 (s, 2H), 2.58 (m, 1H), 1.47 (m, 1H) and 0.00 (s, 9H).

Step 2: (1S,3S,4S)-3-(benzyloxy)-4-(benzyloxymethyl)cyclopentanol (23)

To a solution of ((1R,4S)-4-(benzyloxy)-3-(benzyloxymethyl)cyclopent-2-enyloxy)trimethylsilane (22) (478.00 g, 1.2494 mol) in tetrahydrofuran (9.6 L), Pd, 5 wt % on barium sulfate (265.9 g, 0.1249 mol) was added and the mixture was stirred under 100 psi of hydrogen at ambient temperature for 18 hours, stirring at 200 rpm. HPLC analysis after 18 hours indicated consumption of starting material. The reaction mixture was filtered through a medium frit funnel and the bed was washed with tetrahydrofuran (2000 mL). The filtrate was concentrated, yielding a yellow oil. The resulting oil was taken up in ethyl acetate (2000 mL) to which 2.0 M of hydrochloric acid in water (2000 mL) was added, and the biphasic mixture was stirred for 1 hour. The organic layer was separated and extracted once with saturated sodium bicarbonate in water (2000 mL), twice with 2.0 M of sodium hydroxide in Water (2000 mL) and finally with saturated sodium chloride in water (2000 mL). The organic layer was concentrated to give a brown oil (344 g, 88%) which was used without further purification. $^1$H NMR (300 MHz, CD3OD, δ): 7.18 (m, 10H), 4.38 (m, 4H), 4.12 (m, 1H), 3.85 (t, 1H), 3.68 (m, 1H), 3.44 (m, 1H), 2.00 (m, 3H), 1.75 (m, 1H) and 1.42 (m, 1H).

Step 3: (1R,3S,4S)-3-(benzyloxy)-4-(benzyloxymethyl)cyclopentanol (24)

To a solution of (1S,3S,4S)-3-(benzyloxy)-4-(benzyloxymethyl)cyclopentanol (23) (340.00 g, 1088.3 mmol) in methylene chloride (3400 mL) and triethylamine (455.08 mL, 3265.0 mmol) at 0° C., was added methanesulfonyl chloride (92.661 mL, 1197.2 mmol) slowly under a blanket of nitrogen, maintaining a temperature of less than 10° C. The reaction was allowed to warm to ambient temperature and stirred for 1 hour. HPLC indicated complete consumption of starting material. The reaction mixture was cooled to 0° C. and quenched with water (1700 mL) maintaining a temperature of less than 10° C. The organics were separated and extracted twice with water (1700 mL) and twice with saturated sodium bicarbonate in water (1700 mL). Sodium sulfate (50 g) was added and the mixture stirred for 10 minutes. The slurry was filtered and the filtrate concentrated to give a brown oil. The oil was taken up in tetrahydrofuran (3400 m) to which tetrabutylammonium acetate (656.28 g, 2176.7 mmol) was added and the mixture was stirred at ambient temperature for 20 hours. HPLC analysis indicated complete consumption of starting material. The reaction mixture was concentrated to ~2 volumes (700 mL), and ethyl acetate (3400 mL) was added and mixture was extracted three times with water (1700 mL) and once with saturated sodium chloride in water (1700 mL). The organics were concentrated and the resulting residue was eluted through a plug of silica gel (1 kg) with 0-20% ethyl acetate/hexane [ethyl acetate (4 L)+ hexane (16 L)]. The desired fractions were combined and concentrated to give a brown residue. To the resulting residue, methanol (4000 mL) was added followed by a mixture of sodium hydroxide (130.59 g, 3265.0 mmol) in water (2000 mL), and the reaction mixture was stirred at ambient temperature for 1 hour. HPLC analysis indicated complete consumption of starting material. The majority of the methanol in the reaction mixture was concentrated and water (1700 mL) was added. The mixture was extracted three times with ethyl acetate (3×1700 mL). The combined organics were washed with saturated sodium chloride in water (1700 mL) and dried over sodium sulfate (50 g). The resulting slurry was filtered and concentrated to give a light brown oil (238 g, 70%). $^1$H NMR (300 MHz, CD3OD, δ): 7.28 (m, 10H), 4.50 (m, 3H), 4.38 (m, 2H), 4.12 (t, 1H), 3.70 (m, 1H), 3.45 (m, 1H), 2.52 (m, 1H), 2.11 (m, 1H) and 1.75 (m, 3H).

Step 4: 4-((1R,3S,4S)-3-(benzyloxy)-4-(benzyloxymethyl)cyclopentyloxy)-6-chloropyrimidine (25)

At 0° C., under a blanket of nitrogen, to a solution of (1R,3S,4S)-3-(benzyloxy)-4-(benzyloxymethyl)cyclopentanol (24) (226.500 g, 725.026 mmol) in tetrahydrofuran (1150 mL) was added NaH, 60% in mineral oil (86.995 g, 2175.1 mmol) portionwise, maintaining a temperature of less than 10° C. A solution of 4,6-dichloropyrimidine (118.81 g, 797.53 mmol) in tetrahydrofuran (1150 mL) was then added over 30 minutes maintaining a temperature of less than 5° C. The mixture was allowed to warm to ambient temperature and stirred for 24 hours. HPLC analysis indicated that the reaction mixture contained 74% starting material. The reaction mixture was quenched with a mixture of water (1150 mL) and saturated ammonium chloride in water (1150 ml), maintaining a temperature of less than 10° C. The tetrahydrofuran layer was separated and concentrated to ~2 volumes (500 mL). The aqueous layer was extracted twice with ethyl acetate (1150 mL). The organic layers were combined and washed twice with water (1150 mL) and once with saturated sodium chloride in water (1150 mL). The organics were then concentrated. The residue was taken up in tetrahydrofuran (2300 mL) and cooled to 0° C. under a blanket of nitrogen. NaH, 60% in mineral oil (86.995 g, 2175.1 mmol) was added portionwise maintaining a temperature of less than 10° C. Mixture was allowed to warm to ambient temperature and stirred for 16 hours. HPLC analysis indicated reaction was complete. The reaction mixture was quenched with a mixture of water (1150 mL) and saturated ammonium chloride in water (1150 mL). The tetrahydrofuran layer was separated and concentrated to ~2 volumes (500 mL). The aqueous layer was extracted twice with ethyl acetate (1150 mL). The organic layers were combined and washed twice with water (1150 mL) and once with saturated sodium chloride in water (1150 ml). The organics were then concentrated to give the crude intermediate 4-((1R,3S,4S)-3-(benzyloxy)-4-(benzyloxymethyl)cyclopentyloxy)-6-chloropyrimidine. This crude reaction mixture was taken in to the next step without further purification.

Step 5: (1S,2S,4R)-4-(6-chloropyrimidin-4-yloxy)-2-(hydroxymethyl)cyclopentanol (26)

The crude intermediate 4-((1R,3S,4S)-3-(benzyloxy)-4-(benzyloxymethyl)cyclopentyloxy)-6-chloropyrimidine (25) was taken up in methylene chloride (3000 mL) and the mixture was cooled to 0° C. 1.0 M of Trichloro-borane in methylene chloride (1087.538 mL, 1087.538 mmol) was added slowly maintaining <10° C. The resulting mixture was allowed to stir for 1 hour at 0° C. HPLC analysis indicated consumption of starting material. The reaction mixture was added slowly to saturated sodium bicarbonate in water (2300 mL) and the biphasic mixture was allowed to stir for 20 minutes. The methylene chloride layer was separated and the aqueous extracted twice with methylene chloride (2300 mL). The organics were combined and concentrated. The residue was purified by eluting through a silica gel (1 kg) plug with 50 to 100% ethyl acetate hexane (hexane (6 L)+ ethyl acetate (14 L). The desired fractions were combined and concentrated to give a red solid (124 g, 70%). $^1$H NMR (300 MHz, CD3OD, δ): 8.58 (s, 1H), 6.91 (s, 1H), 5.61 (m, 1H), 4.39 (t, 1H), 3.75 (m, 1H), 3.61 (m, 1H), 2.25 (m, 3H) and 2.00 (m, 2H)

Step 6: (1S,2S,4R)-4-(6-((1R,2S)-5-chloro-2-methoxy-2,3-dihydro-1H-inden-1-ylamino)pyrimidin-4-yloxy)-2-(hydroxymethyl)cyclopentanol (27)

To a 500 ml Parr pressure vessel was added (1S,2S,4R)-4-(6-chloropyrimidin-4-yloxy)-2-(hydroxymethyl)cyclopentanol (26) (25.00 g, 102.2 mmol) in N-methylpyrrolidinone (200 mL). To this mixture was added (1R,2S)-5-chloro-2-methoxy-2,3-dihydro-1H-inden-1-amine hydrochloride (31.10 g, 132.8 mmol) followed by N,N-diisopropylethylamine (88.99 mL, 510.9 mmol). The vessel was then sealed, pressurised with 30 psi of nitrogen and heated to 130° C. for 22 hours. The pressure increased to 50 psi when the reaction reached temperature and held during the course of the reaction. After 22 hours the reaction was cooled to ambient temperature and the pressure was vented. Methylene chloride (250 mL) was added to the reaction mixture and this was then extracted with saturated sodium bicarbonate in water (250 mL). The organic layer was then extracted four times with water (250 mL) and once with saturated sodium chloride in water (250 mL). The organic layer was then dried over sodium sulfate (7.5 g), filtered and concentrated. To the black semisolid oil was added acetonitrile (250 mL) and the mixture was stirred for 2 hours at ambient temperature. During this time a beige solid precipitated and was filtered and dried under reduced pressure at 40° C. for 16 hours. A light biege solid was afforded (17 g, 41%). $^1$H NMR (300 MHz, CD3OD, δ): 8.19 (s, 1H), 7.25 (s, 1H), 7.18 (m, 2H), 5.97 (s, 1H), 5.58 (m, 1H), 5.30 (m, 1H), 4.41 (m, 1H), 4.22 (m, 1H), 3.76 (m, 1H), 3.61 (m, 1H), 3.30 (s, 3H), 3.05 (m, 2H), 2.30 (m, 2H) and 1.97 (m, 3H).

Step 7: ((1S,2S,4R)-4-(6-((1R,2S)-5-chloro-2-methoxy-2,3-dihydro-1H-inden-1-ylamino)pyrimidin-4-yloxy)-2-hydroxycyclopentyl)methyl sulfamate (I-216)

(1S,2S,4R)-4-(6-((1R,2S)-5-Chloro-2-methoxy-2,3-dihydro-1H-inden-1-ylamino)pyrimidin-4-yloxy)-2-(hydroxymethyl)cyclopentanol (27) (85.00 g, 209.4 mmol) was dissolved in N-methylpyrrolidinone (510 mL) in a 3 L reactor. To this solution was added (4-aza-1-azoniabicyclo[2.2.2]oct-1-ylsulfonyl)(tert-butoxycarbonyl)azanide-1,4-diazabicyclo[2.2.2]octane (1:1) hydrochloride (prepared as described in Example 6) (368 g, 838 mmol) in one portion followed by the slow addition of acetonitrile (255 mL). The resultant thick slurry was stirred at ambient temperature for 3 hours. Upon reaction completion, water (595 mL) was added slowly at ambient temperature. To the resulting mixture, ethyl acetate (1.70 L) was added. The organic layer was separated and washed twice with water (2×595 mL) and once with saturated sodium chloride in water (595 mL). The combined aqueous layers were extracted three times with ethyl acetate (850 mL). The combined organic layers were dried over sodium sulfate (20 g), filtered and concentrated. The residue was taken up in acetonitrile (680 mL) and the resulting solution cooled to a temperature of less than 5° C. 12.0 M Hydrochloric acid in water (255 mL, 3060 mmol) was added slowly maintaining an internal temperature of less than 10° C. and the resulting mixture was stirred at ambient temperature for 13 hours. HPLC indicated no Boc protected intermediate remaining. The reaction mixture was added slowly to a mixture of saturated sodium carbonate in water (850 ml) and water (850 mL) maintaining <20° C. Ethyl acetate (850 mL) was then added. The organic layer was separated and extracted twice with water (850 mL) and once with saturated sodium chloride in water (850 mL). The aqueous layers were combined and extracted twice with ethyl acetate (850 mL). The organics were combined and dried over sodium sulfate (20 g), filtered and concentrated. The resulting residue was dissolved in methylene chloride (170 mL) and eluted through a plug of silica (1 Kg) with 4 L of methylene chloride, 4 L of methylene chloride/ethyl acetate (1:1) and finally 8 L ethyl acetate. The desired fractions were combined and concentrated to give a yellow semi-solid (71 g), containing residual NMP. $^1$H NMR (300 MHz, CD3OD, δ): 8.19 (s, 1H), 7.25 (s, 1H), 7.18 (m, 2H), 5.97 (s, 1H), 5.58 (m, 1H), 5.35 (m, 1H), 4.35 (m, 2H), 4.15 (m, 2H), 3.30 (s, 3H), 3.05 (m, 2H), 2.51 (m, 1H), 2.30 (m, 2H) and 2.00 (m, 2H).

Step 8: Preparation of ((1S,2S,4R)-4-(6-((1R,2S)-5-chloro-2-methoxy-2,3-dihydro-1H-inden-1-ylamino)pyrimidin-4-yloxy)-2-hydroxycyclopentyl)methyl sulfamate hydrochloride Form I (I-216 HCl Form I)

In a 3-neck, 3 L reactor, the crude I-216 from step 7 (142.00 g, 292.81 mmol was slurried in isopropyl alcohol (710 mL) and the mixture was heated to 60° C. for 20 minutes. 6.0 M hydrochloric acid in water (97.604 mL, 585.62 mmol) was then added very slowly and mixture stirred at 60° C. for 10 minutes. Complete dissolution was observed after 10 ml of the 6M HCl was added, with an exotherm of 7° C. The reaction mixture was cooled to 50° C. and seeded with previously prepared I-216 HCl Form I (prepared as described in Example 7 below) (100 mg). Solids began to slowly precipitate and this slurry was allowed to stir at 50° C. for 60 minutes. Isopropyl acetate (1420 mL) was added slowly over 1 hour maintaining >45° C. The mixture was allowed to cool to ambient temperature and stirred for 2 hours, cooled to <5° C. and stirred for 2 hours. The solids were filtered and the bed was gravity washed with acetic acid, 1-methylethyl ester (710 mL). Solids were dried under reduced pressure at 45° C. for 16 hours, yielding white solids (113.5 g, 51% over 2 steps). $^1$H NMR (300 MHz, CD3OD, δ): 8.48 (s, 1H), 7.33 (5, 1H), 7.22 (m, 2H), 6.30 (m, 1H), 5.82 (m, 1H), 5.31 (m, 1H), 4.44 (t, 1H), 4.30 (m, 2H), 4.18 (m, 1H), 3.35 (s, 3H), 3.15 (m, 2H), 2.55 (m, 1H), 2.38 (m, 1H) and 2.17 (m, 3H). LCMS: $R_f$=9.30 mins, ES$^+$=485 (FA). XRPD data for Form I is shown in FIG. 4. DSC data for Form I is shown in FIG. 5, and TGA data for Form I is shown in FIG. 6.

Example 6. Synthesis of (4-aza-1-azoniabicyclo [2.2.2]oct-1-ylsulfonyl)(tert-butoxycarbonyl)azanide-1,4-diazabicyclo[2.2.2]octane (1:1) hydrochloride Chlorosulfonyl isocyanate (45.2 Kg, 319.4 mol) was added to toluene (194.2 Kg) and the resulting solution cooled to between about 0-6° C. A solution of tert-butyl alcohol (23.6 Kg, 318.4 mol) in toluene (48.0 Kg) was then added over a period of 90 minutes, maintaining a temperature of between about 0-6° C. The mixture was then stirred until consumption of tert-butyl alcohol was complete (approximately 80 minutes). A solution of triethylenediamine (DABCO, 71.4 Kg, 636.5 mol) in toluene (293.0 Kg) was then added to the mixture over a period of 2.5 hours, maintaining a temperature of between about 0-6° C. The mixture was then warmed to 20-25° C. and stirred for 8 hours. The solid product was isolated by centrifugal filtration under a nitrogen atmosphere and washed with toluene (180.8 Kg) and then tert-butyl methyl ether (51.0 gallons) and spun until no further liquors were seen to be expelled (approximately 60 minutes). The solids were then further dried under vacuum to afford 132.9 Kg of (4-aza-1-azoniabicyclo[2.2.2]oct-1-ylsulfonyl)(tert-butoxycarbonyl)azanide-1,4-diazabicyclo[2.2.2]octane (1:1) hydrochloride.

Example 7. Synthesis of Seed I-216 Hydrochloride Salt Form I Used in Example 5

Step 1: tert-butyl [({(1S,2S,4R)-4-[(6-{[(1R,2S)-5-chloro-2-methoxy-2,3-dihydro-1H-inden-1-yl] amino}pyrimidin-4-yl)oxy]-2-hydroxycyclopentyl}methoxy)sulfonyl]carbamate To a solution of (4-aza-1-azoniabicyclo[2.2.2]oct-1-ylsulfonyl)(tert-butoxycarbonyl)azanide-1,4-diazabicyclo[2.2.2] octane (1:1) hydrochloride (43.4 g, 98.6 mmol) in acetonitrile (30 mL), in a 500 mL reactor, was added (1S,2S,4R)-4-(6-((1R,2S)-5-chloro-2-methoxy-2,3-dihydro-1H-inden-1-ylamino)pyrimidin-4-yloxy)-2-(hydroxymethyl) cyclopentanol (27) (10 g, 24.6 mmol) in N-methylpyrrolidinone (60 mL). The resultant thick slurry was stirred at ambient temperature for 3 hours. Upon reaction completion, water (66.6 mL) was added slowly at ambient temperature. To the resulting mixture, ethyl acetate (66.7 mL) was added. The aqueous layer was extract three times with ethyl acetate (3×66.6 mL). The combined organic layers were washed once with water (66.7 mL) and once with saturated sodium chloride in water (66.7 mL). The combined organic layers were dried over magnesium sulfate (3 g), filtered and concentrated. This product was taken on to the next step without further purification.

Step 2: Preparation of ((1S,2S,4R)-4-(6-((1R,2S)-5-chloro-2-methoxy-2,3-dihydro-1H-inden-1-ylamino) pyrimidin-4-yloxy)-2-hydroxycyclopentyl)methyl sulfamate hydrochloride Form I (I-216 HCl Form I)

The residue from Step 1 (10 g) was taken up in acetonitrile (81.5 mL) and the resulting solution cooled to a temperature of less than 5° C. 12.0 M Hydrochloric acid (27.7 mL, 904 mmol) was added slowly maintaining an internal temperature of less than 10° C. and the resulting mixture was stirred at 0° C. for 4 hours then warmed to room temperature and stirred for 15 h. HPLC indicated no Boc protected intermediate remaining. To the reaction mixture was added water (20 mL, 1110 mmol) and the temperature was increased to 60° C. Once at temperature the reaction was seeded with material prepared as described in Example 8. The seed held and the reaction was allowed to cool slowly to room temperature and stir for 16 h. The reaction was filtered and washed with water (66 mL) and dried overnight under reduced pressure. This gave a white solid (5.3 g, 9.8 mmol) of the product in 60% yield $^1$H NMR (300 MHz, CD3OD, δ): 8.19 (s, 1H), 7.25 (s, 1H), 7.18 (m, 2H), 5.97 (s, 1H), 5.58 (m, 1H), 5.35 (m, 1H), 4.35 (m, 2H), 4.15 (m, 2H), 3.30 (s, 3H), 3.05 (m, 2H), 2.51 (m, 1H), 2.30 (m, 2H) and 2.00 (m, 2H).

Example 8. Synthesis of Seed I-216 Hydrochloride Salt Form I Used in Example 7 tert-Butyl [({(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methoxy)sulfonyl]carbamate (1 g; prepared in a similar manner to that described in Example 7, Step 1) was taken up in acetonitrile (8.12 mL) and the resulting solution cooled to a temperature of less than 5° C. 12.0 M Hydrochloric acid (2.7 mL, 89 mmol) was added slowly maintaining an internal temperature of less than 10° C. and the resulting mixture was stirred at 0° C. for 4 hours then warmed to room temperature and stirred for 15 h. HPLC indicated no Boc protected intermediate remaining. To the reaction mixture was added a small amount of water and sodium bicarbonate to neutralize, but this amount did not completely neutralize the solution. The reaction mixture was concentrated at 40° C. and then the solution was cooled to room temperature and stirred overnight. Further water was added and the solution was stirred an hour longer. The reaction was filtered and washed with water and dried overnight under reduced pressure to gave a white solid (0.598 g, 1.15 mmol) of the product in 68% yield $^1$H NMR (300 MHz, CD3OD, δ): 8.19 (s, 1H), 7.25 (s, 1H), 7.18 (m, 2H), 5.97 (s, 1H), 5.58 (m, 1H), 5.35 (m, 1H), 4.35 (m, 2H), 4.15 (m, 2H), 3.30 (s, 3H), 3.05 (m, 2H), 2.51 (m, 1H), 2.30 (m, 2H) and 2.00 (m, 2H).

This white solid (250 mg, 0.479 mmol) was suspended in isopropyl alcohol (2.5 mL, 32.6 mmol) and heated to 60° C. 8.0 M HCl in water (0.120 mL, 0.959 mmol) was added and some dissolution occurred. After 15 minutes, the heating was removed and the suspension was cooled to room temperature and stirred overnight. The solid was filtered and washed with 5% aq. IPA and dried overnight under reduced pressure. This afforded the title compound (0.204 g, 0.391 mmol) in 81.6% yield. $^1$H NMR (300 MHz, CD3OD, δ): 8.19 (s, 1H), 7.25 (s, 1H), 7.18 (m, 2H), 5.97 (s, 1H), 5.58 (m, 1H), 5.35 (m, 1H), 4.35 (m, 2H), 4.15 (m, 2H), 3.30 (s, 3H), 3.05 (m, 2H), 2.51 (m, 1H), 2.30 (m, 2H) and 2.00 (m, 2H).

Example 9. Preparation of ((1S,2S,4R)-4-(6-((1R,2S)-5-chloro-2-methoxy-2,3-dihydro-1H-inden-1-ylamino)pyrimidin-4-yloxy)-2-hydroxycyclopentyl) methyl sulfamate hydrochloride Form II (I-216 HCl Form II)

I-216 HCl Form I (0.5 g, prepared as described in Example 5 above) was slurried in water (10 mL) at ambient temperature for 18 h. The resulting solids were filtered, washed with water (2.5 mL) and dried under reduced pressure at ambient temperature for 16 h. This afforded Form II of I-216 HCl as a white solid (0.45 g) in 90% yield. $^1$H NMR (300 MHz, CD$_3$OD, δ): 8.35 (s, 1H), 7.30 (s, 1H), 7.21 (m, 2H), 6.17 (m, 1H), 5.65 (m, 1H), 5.35 (m, 1H), 4.41 (t, 1H), 4.30 (m, 2H), 4.17 (m, 1H), 3.36 (s, 3H), 3.10 (m, 2H), 2.55 (m, 1H), 2.35 (m, 1H) and 2.10 (m, 3H). LCMS: $R_t$=9.29 mins, ES$^+$=485 (FA). XRPD data for Form II is shown in FIG. 10.

Example 10. In Vivo Tumor Pharmacodynamic Model

HCT116 tumor cells (2×10$^6$) (ATCC #CCL-247) in 100 μL phosphate buffered saline were aseptically injected into the subcutaneous space in the right dorsal flank of female Ncr nude mice (age 5-8 weeks, Charles River) using a 26-gauge needle. Beginning on day 7 after inoculation, tumors were measured twice weekly using a vernier caliper. Tumor volumes were calculated using standard procedures (0.5×(length×width$^2$)). When the tumors reached a volume of approximately 3-700 mm$^3$ mice were randomized into groups and injected subcutaneously with compound inhibitor (200 μL) at various doses. Tumors were harvested and crushed in Covaris bags and then transferred to glass tubes on dry ice for sonication in the Covaris E200. Mammalian protein extraction reagent (MPER) lysis buffer (Pierce, 78501) was supplemented with the following (final concentrations): 1× protease inhibitor cocktail set (Calbiochem, 539134), 5 mM o-phenanthroline in dimethyl sulfoxide (DMSO) (Sigma, #P1294 and Sigma DMSO #D2650), 10 mM iodoacetimide (Sigma), 2 mM sodium orthovanadate (Sigma, #S6508), 25 mM sodium fluoride, and 25 mM β-glycerophosphate. Cold lysis buffer (300-800 μL) was added to the tumors just before sonication. The sonication steps were: 10 seconds, 1% 500 mV 50, 20 seconds, 20% 500 mV 50, 20 seconds, 10% 500 mV 50. After sonication samples were placed on wet ice, poured into Eppendorf tubes and spun at 14000 rpm for 20 min at 4° C. in a microfuge. Supernatants were transferred to new tubes and protein concentrations were determined using the Pierce bicinchoninic acid (BCA) reagents and protein standards. Tumor lysates were stored at −80° C.

For quantitative analysis of neddylated cullins the procedure was as follows: 20 μg of tumor lysate with lithium dodecyl sulfate (LDS) loading buffer and sample reducing agent (Invitrogen NP0007 and NP0004) was loaded onto 4-12% bis-tris gels, 1.5 mM, 10 well gels (Invitrogen NP0315Box). Gels were run at 150V in 2-(N-morpholino) ethane sulfonic acid (MES) running buffer (Invitrogen NP0002). Gels were cut at appropriate molecular weight marker and transferred to PVDF-FL (Millipore, IPFL00010) using a semi dry transfer apparatus (Amersham Biosciences, TE70). After transfer, membranes were blocked in Odyssey blocker (LI-COR Biosciences #927-40000), then incubated with primary antibodies in Odyssey blocker+0.1% Tween-20 (Sigma #P7949) overnight at 4 degrees. Membranes were washed three times in tris buffered saline with Tween-20 (TBST) and then incubated with Alexa Fluor 680 labeled goat anti-rabbit immunoglobulin G, heavy and light chain (IgG (H+L)) antibody (Molecular Probes Cat # A-21109). After 1 hour incubation with secondary antibody in the dark, membranes were washed 5 times with TBST and once with tris buffered saline (TBS), protected from light. Membranes were dried for at least one hour and then scanned with the Odyssey Infrared Imaging System (LI-COR Biosciences). The following primary antibody was used: Anti-Nedd-8 (MIL10 clone 52-9-5, developed with Epitomics, dilution of 1:4000). Secondary antibody was used at 1:2000. Quantitation of signals on Western blots was performed with the Odyssey, software.

The patent and scientific literature referred to herein establishes knowledge that is available to those skilled in the art. Unless otherwise defined, all technical and scientific terms used herein have the same meaning as commonly understood by those skilled in the art to which the invention belongs. The issued patents, applications, and references that are cited herein are hereby incorporated by reference to the same extent as if each was specifically and individually indicated to be incorporated by reference. In the case of inconsistencies, the present disclosure, including definitions, is intended to control.

While a number of embodiments of the invention have been described, it is apparent that the provided basic examples may be altered to convey other embodiments, which utilize the compounds, methods, etc. of the invention. It will thus be appreciated that the scope of the invention has been represented herein by way of example and is not intended to be limited by the specific embodiments.

What is claimed is:

1. A chemical entity comprising a hydrochloride salt of the compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate or a pharmaceutically acceptable solvate thereof, wherein said chemical entity is substantially crystalline Form II.

2. A prodrug of a chemical entity, wherein:
the chemical entity is the compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate or a pharmaceutically acceptable salt thereof; and
the prodrug is a carbamate or amide of an NH group of the chemical entity, or an ether or ester of an OH group of the chemical entity.

3. A composition comprising the chemical entity of claim 1, and a pharmaceutically acceptable carrier.

4. The composition of claim 3 suitable for oral administration.

5. The chemical entity of claim 1, wherein at least 70% by weight is crystalline Form II.

6. The chemical entity of claim 1, wherein at least 80% by weight is crystalline Form II.

7. The chemical entity of claim 1, wherein at least 90% by weight is crystalline Form II.

8. The chemical entity of claim 1, wherein at least 95% by weight is crystalline Form II.

9. The chemical entity of claim 1, wherein Form II is characterized by an x-ray powder diffraction (XRPD) pattern having peaks at 2θ angles of 8.7°, 15.2°, 15.7°, 19.6°, and 24.2°, wherein each 2θ angle value is ±0.2°.

10. The chemical entity of claim 9, wherein Form II is characterized by an XRPD pattern having peaks at 2θ angles of 4.3°, 8.7°, 15.2°, 15.7°, 19.6°, 20.0°, 20.8°, 22.5°, 23.1°, and 24.2°, wherein each 2θ angle value is ±0.2°.

11. The chemical entity of claim 9, wherein Form II is characterized by an XRPD pattern having peaks at 2θ angles of 4.3°, 8.7°, 12.4°, 14.5°, 15.2°, 15.7°, 17.3°, 18.2°, 18.5°, 19.6°, 20.0°, 20.8°, 22.0°, 22.5°, 23.1°, 24.2°, 24.7°, 25.7°, 28.2° and 29.4°, wherein each 2θ angle value is ±0.2°.

12. The chemical entity of claim 1, wherein Form II is characterized by an x-ray powder diffraction (XRPD) pattern having a reference peak with a 2θ angle of 8.7±0.3°, and having peaks at 2θ angles of −4.4°, 6.5°, 7.0°, 10.9°, 11.3°, 12.1°, 13.8°, 14.4°, and 15.5° relative to the reference peak.

13. The chemical entity of claim 1, wherein Form II is characterized by an x-ray powder diffraction (XRPD) pattern having a reference peak with a 2θ angle of 8.7±0.3°, and having peaks at 2θ angles of −4.4°, 3.7°, 5.8°, 6.5°, 7.0°, 8.6°, 9.5°, 9.8°, 10.9°, 11.3°, 13.3°, 13.8°, 14.4°, 15.5°, 16.0°, 17.0°, 19.5° and 20.7° relative to the reference peak.

14. The chemical entity of claim 1, wherein Form II is characterized by an x-ray powder diffraction (XRPD) pattern substantially as shown in FIG. 10.

15. A composition comprising the prodrug of claim 2 and a pharmaceutically acceptable carrier.

\* \* \* \* \*